(12) United States Patent
Kim et al.

(10) Patent No.: US 10,102,444 B2
(45) Date of Patent: Oct. 16, 2018

(54) OBJECT RECOGNITION METHOD AND APPARATUS BASED ON WEAKLY SUPERVISED LEARNING

(71) Applicant: Lunit Inc., Seoul (KR)

(72) Inventors: Hyo Eun Kim, Seongnam-si (KR); Sang Heum Hwang, Seoul (KR)

(73) Assignee: Lunit Inc., Seoul (KR)

( * ) Notice: Subject to any disclaimer, the term of this patent is extended or adjusted under 35 U.S.C. 154(b) by 72 days.

(21) Appl. No.: 15/378,039

(22) Filed: Dec. 14, 2016

(65) Prior Publication Data

US 2018/0144209 A1    May 24, 2018

(30) Foreign Application Priority Data

Nov. 22, 2016 (KR) .................. 10-2016-0156035

(51) Int. Cl.
*G06K 9/46* (2006.01)
*G16H 50/20* (2018.01)
(Continued)

(52) U.S. Cl.
CPC ............ *G06K 9/4671* (2013.01); *G06N 3/04* (2013.01); *G06N 3/0454* (2013.01); *G06N 3/08* (2013.01);
(Continued)

(58) Field of Classification Search
None
See application file for complete search history.

(56) References Cited

U.S. PATENT DOCUMENTS 9,373,059 B1 * 6/2016 Heifets ............... G06F 19/16
9,536,293 B2 * 1/2017 Lin ..................... G06T 7/0002
(Continued)

FOREIGN PATENT DOCUMENTS

| KR | 10-2016-0061856 A | 6/2016 |
| KR | 10-2016-0096460 A | 8/2016 |
| KR | 10-2018-0027887 A | 3/2018 |

OTHER PUBLICATIONS

Self-Transfer Learning for Fully Weakly Supervised Object Localization. Hwang et al. Feb. 2016.*
(Continued)

*Primary Examiner* — Delomia L Gilliard
(74) *Attorney, Agent, or Firm* — Studebaker & Brackett PC

(57) ABSTRACT

Provided are an object recognition method and apparatus which determine an object of interest included in a recognition target image using a trained machine learning model and determine an area in which the object of interest is located in the recognition target image. The object recognition method based on weakly supervised learning, performed by an object recognition apparatus, includes extracting a plurality of feature maps from a training target image given classification results of objects of interest, generating an activation map for each of the objects of interest by accumulating the feature maps, calculating a representative value of each of the objects of interest by aggregating activation values included in a corresponding activation map, determining an error by comparing classification results determined using the representative value of each of the objects of interest with the given classification results and updating a CNN-based object recognition model by back-propagating the error.

11 Claims, 17 Drawing Sheets

(51) Int. Cl.
  *G06N 3/04* (2006.01)
  *G06N 3/08* (2006.01)
  *G06T 7/00* (2017.01)
(52) U.S. Cl.
  CPC ........... *G06T 7/0012* (2013.01); *G16H 50/20* (2018.01); *G06T 2207/10004* (2013.01); *G06T 2207/20081* (2013.01); *G06T 2207/20084* (2013.01); *G06T 2207/30096* (2013.01)

(56) References Cited

U.S. PATENT DOCUMENTS

| | | | | |
|---|---|---|---|---|
| 9,760,807 | B2* | 9/2017 | Zhou | G06K 9/66 |
| 9,953,425 | B2* | 4/2018 | Lin | G06T 7/33 |
| 2012/0316421 | A1* | 12/2012 | Kumar | A61B 1/00009 |
| | | | | 600/407 |
| 2015/0036920 | A1* | 2/2015 | Wu | G06N 3/0454 |
| | | | | 382/156 |
| 2016/0328630 | A1* | 11/2016 | Han | G06K 9/6272 |
| 2017/0032222 | A1* | 2/2017 | Sharma | G06K 9/6256 |
| 2017/0262735 | A1* | 9/2017 | Ros Sanchez | G06K 9/6256 |
| 2018/0018757 | A1* | 1/2018 | Suzuki | G06T 3/4053 |
| 2018/0068198 | A1* | 3/2018 | Savvides | G06K 9/3233 |
| 2018/0068207 | A1* | 3/2018 | Szegedy | G06K 9/66 |
| 2018/0130203 | A1* | 5/2018 | Abedini | G06T 7/0012 |
| 2018/0137338 | A1* | 5/2018 | Kraus | G06K 9/00147 |

OTHER PUBLICATIONS

Hwang et al., "Self-Transfer Learning for Fully Weakly Supervised Object Localization", arXiv:1602.01625v1 [cs.CV], Feb. 4, 2016, pp. 1-9, Lunit Inc., Seoul, South Korea.

Kim et al., "Deconvolutional Feature Stacking for Weakly-Supervised Semantic Segmentation", arXiv:1602.04984v3 [cs.CV], Mar. 12, 2016, pp. 1-16, Lunit Inc., Seoul, South Korea.

A Notice of Allowance dated Jun. 29, 2018, which corresponds to Korean Patent Application No. 10-2016-0156035 and is related to U.S. Appl. No. 15/378,039; English translation.

* cited by examiner

FIG. 8
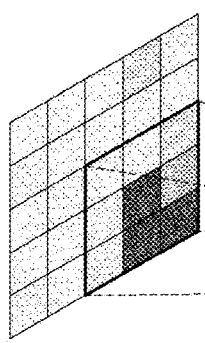
(a)
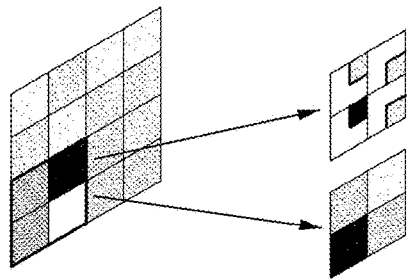
(b)
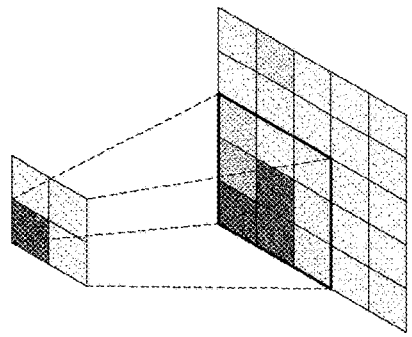
(c)
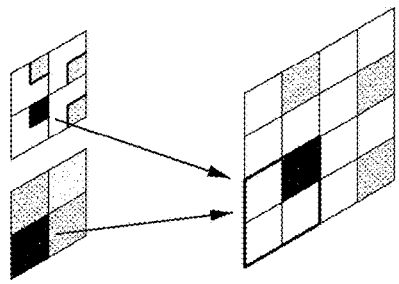
(d)

FIG. 14
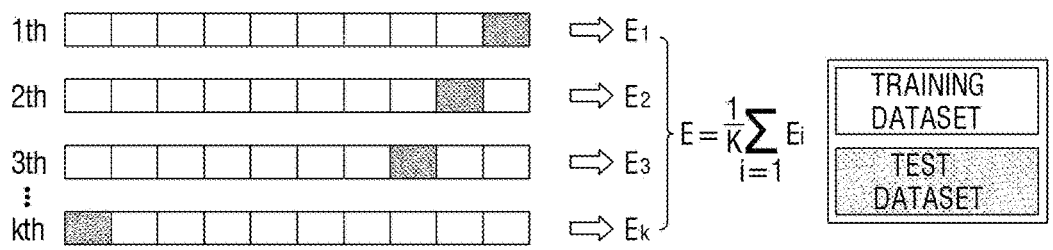
(a)
| PREDICTED VALUE \ OBSERVED VALUE | True | False |
|---|---|---|
| True | TP | FP |
| False | FN | TN |
(b)
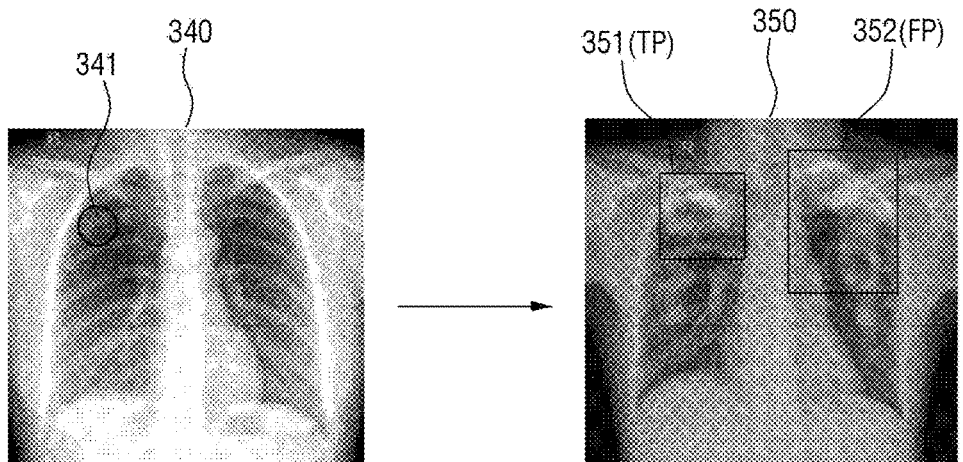
(c)

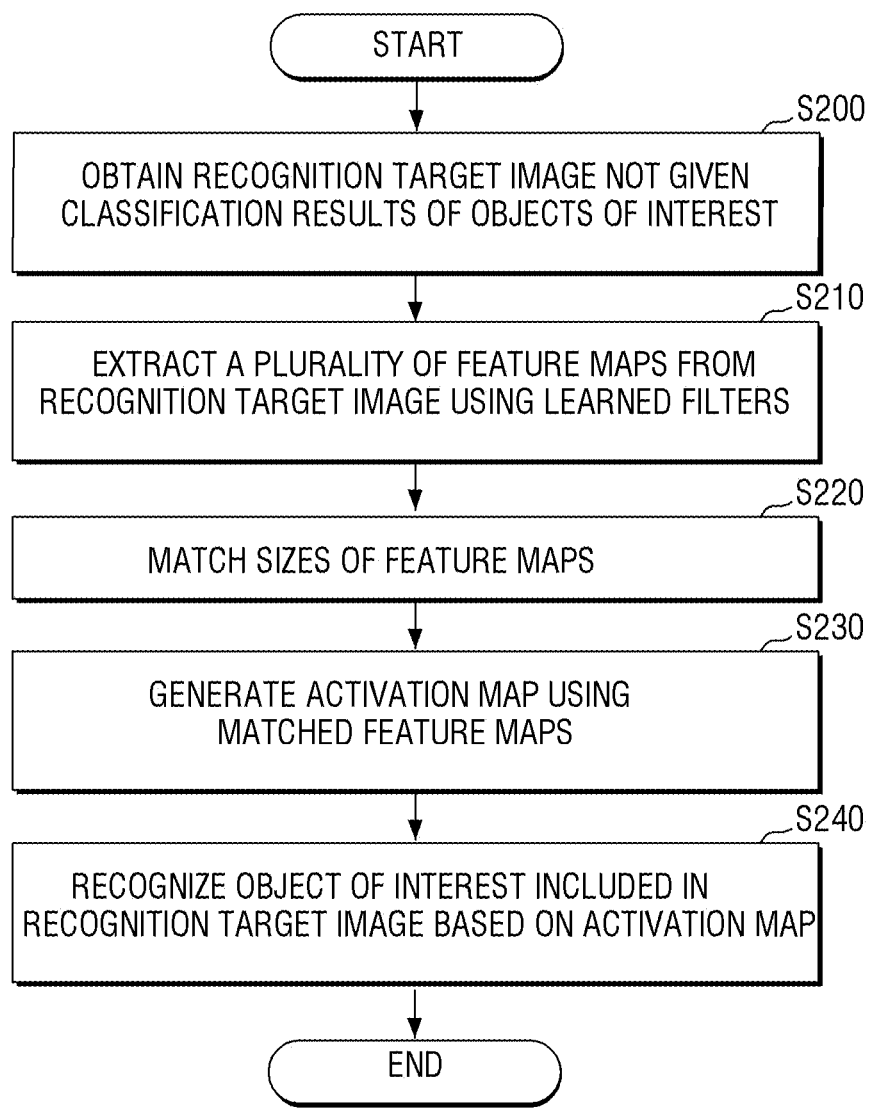

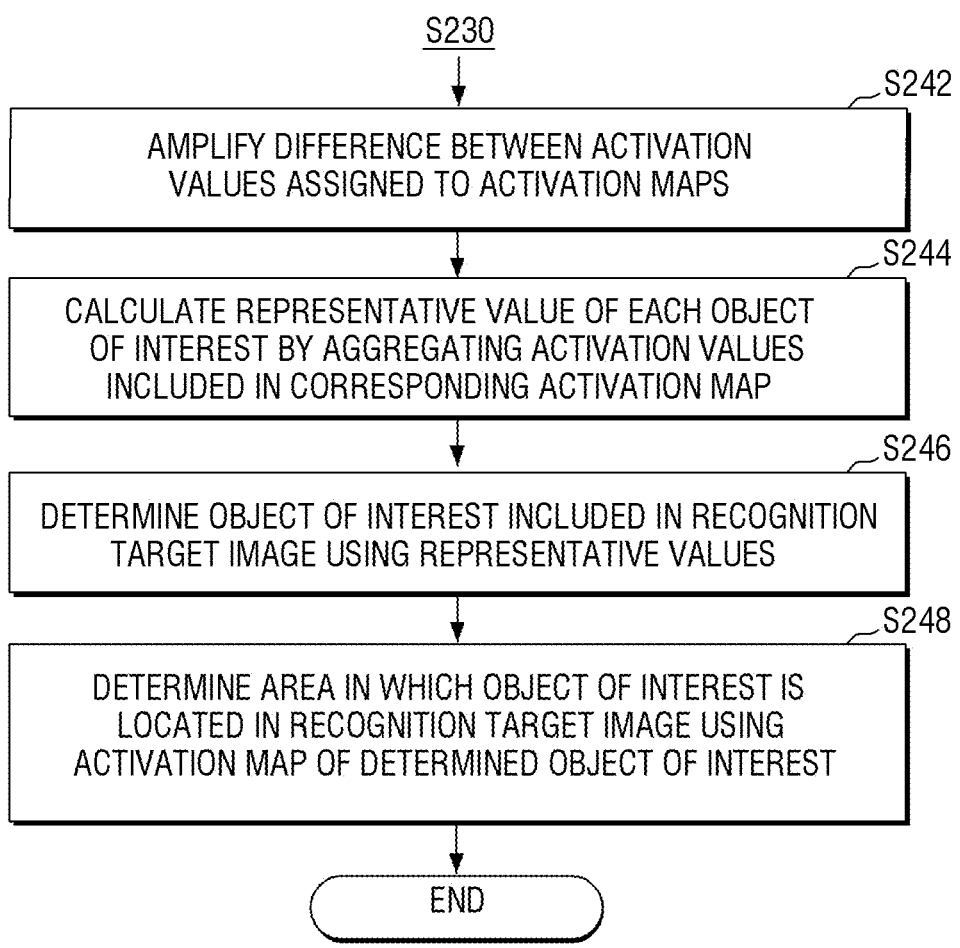

OBJECT RECOGNITION METHOD AND APPARATUS BASED ON WEAKLY SUPERVISED LEARNING

This application claims the benefit of Korean Patent Application No. 10-2016-0156035, filed on Nov. 22, 2016, in the Korean Intellectual Property Office, the disclosure of which is incorporated herein by reference in its entirety.

BACKGROUND

1. Field

The present inventive concept relates to an object recognition method and apparatus based on weakly supervised learning, and more particularly, to an object recognition method and apparatus which determine an object of interest included in a recognition target image using a trained machine learning model and determine an area in which the object of interest is located in the recognition target image.

2. Description of the Related Art

Medical images are one of the important tools for diagnosing and treating patients in modern medicine. In particular, radiographic images of patients are being widely utilized to initially diagnose the patients because they can be acquired rapidly at low cost.

However, it is very difficult even for an expert radiologist to identify the accurate location of a lesion in a patient's radiographic image and diagnose a disease that caused the lesion. This arises from complicated causes such as the loss of information that occurs in the process of converting the three-dimensional structure of the human body into a two-dimensional radiographic image and the limitations of human perception.

To solve the above problem, computer-aided diagnosis (CAD) is being researched by applying various machine learning algorithms that are based on supervised learning.

To predict a pathological diagnosis result, which includes the location of a lesion in a patient's radiographic image, through supervised learning-based machine learning, a radiographic image tagged with the accurate location of a lesion is required. In reality, however, there are not many radiographic images tagged with location information of a lesion. In addition, generating a radiographic image tagged with the location of a lesion needs help from experts such as radiologists. Thus, excessive time and labor are required. For this reason, a technology for predicting a pathological diagnosis result including the location of a lesion in a radiographic image has not been suggested.

Therefore, it is required to come up with a technology for predicting, through machine learning, a pathological diagnosis result including the location of a lesion based on medical image data given only a pathological diagnosis result such as the presence or absence of a lesion or the type of the lesion.

SUMMARY

Aspects of the inventive concept provide an object recognition method and apparatus which can recognize not only a classification result of an object of interest included in a recognition target image but also an area in which the object of interest is located using a training target image given classification results of objects of interest.

Aspects of the inventive concept also provide an object recognition method and apparatus which can recognize not only a classification result of an object of interest included in a recognition target image but also an area in which the object of interest is located using a weakly supervised learning-based object recognition model.

Aspects of the inventive concept also provide an object recognition method and apparatus which can efficiently train an object recognition model based on weakly supervising learning.

However, aspects of the inventive concept are not restricted to the one set forth herein. The above and other aspects of the inventive concept will become more apparent to one of ordinary skill in the art to which the inventive concept pertains by referencing the detailed description of the inventive concept given below.

According to an aspect of the inventive concept, there is provided an object recognition method based on weakly supervised learning, the method comprises training a convolutional neural network (CNN)-based object recognition model using a training target image by using an object recognition apparatus and recognizing an object of interest included in a recognition target image using the trained object recognition model by using the object recognition apparatus, wherein the object recognition model comprises a convolution layer which extracts a plurality of feature maps from the training target image and a deconvolution layer which increases sizes of the feature maps, and a weight matrix of a filter used in the deconvolution layer is obtained by transposing a weight matrix of a filter used in the convolution layer corresponding to the deconvolution layer.

According to another aspect of the inventive concept, there is provided an object recognition method based on weakly supervised learning, the method performed by an object recognition apparatus comprises extracting a plurality of feature maps from a training target image given classification results of objects of interest, generating an activation map for each of the objects of interest by accumulating the feature maps, calculating a representative value of each of the objects of interest by aggregating activation values included in a corresponding activation map, determining an error by comparing classification results determined using the representative value of each of the objects of interest with the given classification results; and updating a CNN-based object recognition model by back-propagating the error.

According to another aspect of the inventive concept, there is provided an object recognition apparatus, the apparatus comprises one or more processors, a network interface, a memory which loads a computer program executed by the processors to perform an object recognition method based on weakly supervised learning and a storage which stores the computer program, wherein the computer program comprises an operation of training a CNN-based object recognition model using a training target image and an operation of recognizing an object of interest included in a recognition target image using the trained object recognition model, wherein the object recognition model comprises a convolution layer which extracts a plurality of feature maps from the training target image and a deconvolution layer which increases sizes of the feature maps, and a weight matrix of a filter used in the deconvolution layer is obtained by transposing a weight matrix of a filter used in the convolution layer corresponding to the deconvolution layer.

According to another aspect of the inventive concept, there is provided an object recognition apparatus, the apparatus comprises one or more processors, a network interface, a memory which loads a computer program executed by the processors to perform an object recognition method based on weakly supervised learning and a storage which stores the computer program, wherein the computer program comprises, an operation of extracting a plurality of feature maps from a training target image given classification results of objects of interest, an operation of generating an activation map for each of the objects of interest by accumulating the feature maps, an operation of calculating a representative value of each of the objects of interest by aggregating activation values included in a corresponding activation map, an operation of determining an error by comparing classification results determined using the representative value of each of the objects of interest with the given classification results and an operation of updating a CNN-based object recognition model by back-propagating the error.

According to another aspect of the inventive concept, there is provided a computer program coupled to a computing device and stored in a recording medium to execute an object recognition method based on weakly supervised learning, the computer program comprises an operation of training a CNN-based object recognition model using a training target image and an operation of recognizing an object of interest included in a recognition target image using the trained object recognition model, wherein the object recognition model comprises a convolution layer which extracts a plurality of feature maps from the training target image and a deconvolution layer which increases sizes of the feature maps, and a weight matrix of a filter used in the deconvolution layer is obtained by transposing a weight matrix of a filter used in the convolution layer corresponding to the deconvolution layer.

According to another aspect of the inventive concept, there is provided a computer program coupled to a computing device and stored in a recording medium to execute an object recognition method based on weakly supervised learning, the computer program comprises an operation of extracting a plurality of feature maps from a training target image given classification results of objects of interest, an operation of generating an activation map for each of the objects of interest by accumulating the feature maps, an operation of calculating a representative value of each of the objects of interest by aggregating activation values included in a corresponding activation map, an operation of determining an error by comparing classification results determined using the representative value of each of the objects of interest with the given classification results; and an operation of updating a CNN-based object recognition model by back-propagating the error.

BRIEF DESCRIPTION OF THE DRAWINGS

These and/or other aspects will become apparent and more readily appreciated from the following description of the embodiments, taken in conjunction with the accompanying drawings in which:

FIG. 8 illustrates operations performed to extract a feature map;

FIG. 14 illustrates an operation of validating an object recognition model, which can be referred to in some embodiments;

FIGS. 15 and 16 illustrate an operation of recognizing an object of interest using a trained object recognition model, which can be referred to in some embodiments; and FIGS. 17 and 18 illustrate experimental results of the inventive concept.

DETAILED DESCRIPTION

Figure 1:
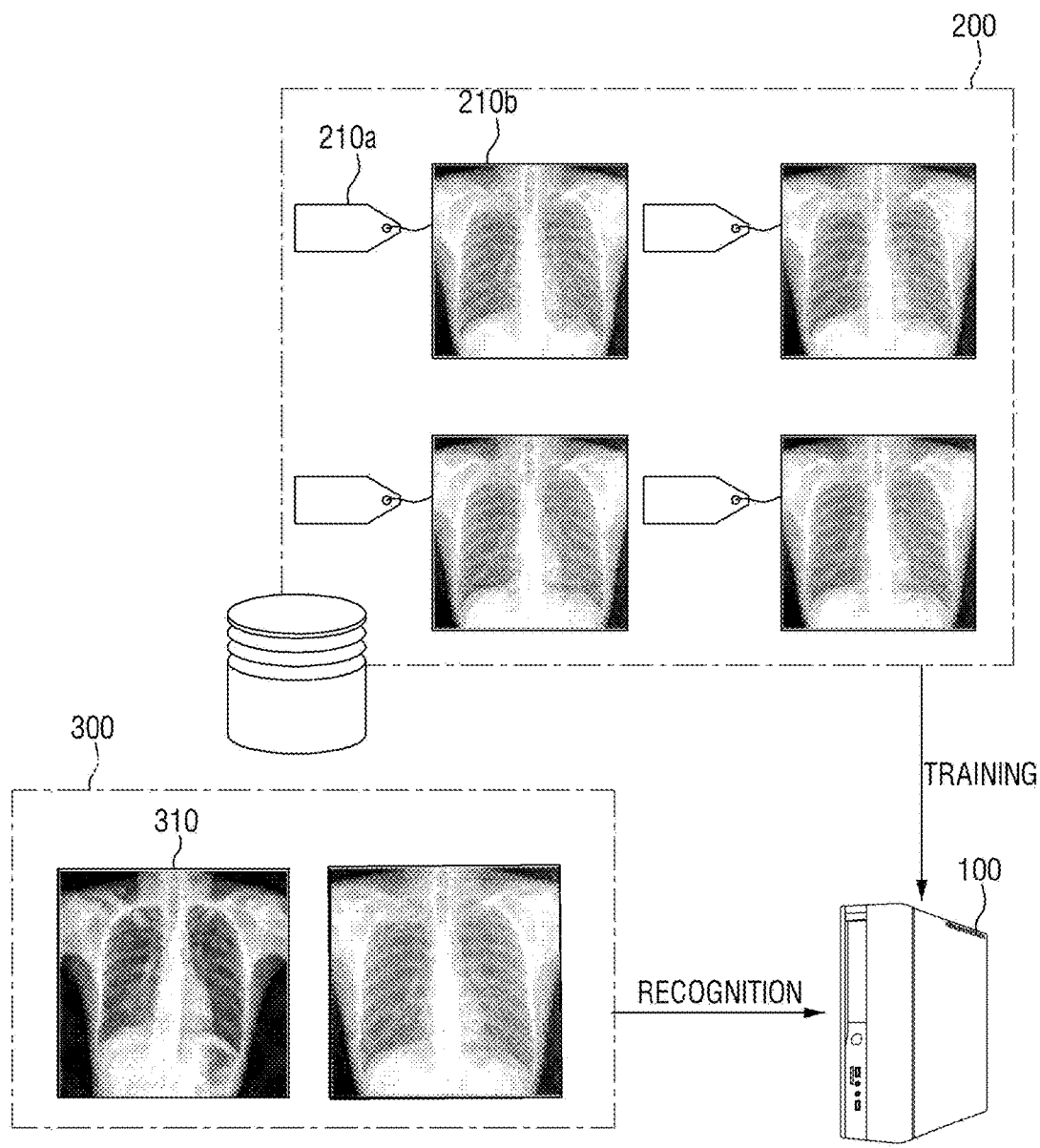
FIG. 1 illustrates the configuration of an object recognition system according to an embodiment.

The present inventive concept will now be described more fully with reference to the accompanying drawings, in which exemplary embodiments of the inventive concept are shown. Advantages and features of the inventive concept and methods of accomplishing the same may be understood more readily by reference to the following detailed description of exemplary embodiments and the accompanying drawings. The inventive concept may, however, be embodied in many different forms and should not be construed as being limited to the embodiments set forth herein. Rather, these embodiments are provided so that this disclosure will be thorough and complete and will fully convey the concept of the invention to those skilled in the art, and the inventive concept will only be defined by the appended claims. Like reference numerals refer to like components throughout the specification.

Unless otherwise defined, all terms (including technical and scientific terms) used herein have the same meaning as commonly understood by one of ordinary skill in the art to which the inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. The terminology used herein is for the purpose of describing particular embodiments only and is not intended to be limiting of the inventive concept. As used herein, the singular forms "a", "an" and "the" are intended to include the plural forms as well, unless the context clearly indicates otherwise.

It will be further understood that the terms "comprises" and/or "comprising," when used in this specification, specify the presence of stated components, steps, and/or operations, but do not preclude the presence or addition of one or more other components, steps, operations, and/or groups thereof.

Hereinafter, the inventive concept will be described in greater detail with reference to the attached drawings.

Object Recognition System

First of all, an object recognition system according to an embodiment will be described.

FIG. 1 illustrates the configuration of an object recognition system according to an embodiment.

Referring to FIG. 1, the object recognition system is a system that performs training based on a training target image given classification results of objects of interest and recognizes an object of interest included in a recognition target image not given the classification results of the objects of interest.

Here, a classification result of an object of interest refers to information about whether an object of interest exists in a given image or information about, e.g., the type of the object of interest included in the given image. In addition, the training refers to a machine learning process and can be used interchangeably with the term "learning."

Moreover, an object of interest refers to an object to be recognized in a given image. For example, if the location of a lesion is to be recognized in a radiographic image, the object of interest may be a lesion that occurred in the body. The type of an object of interest may be defined in advance.

In addition, the term "object recognition," as used herein, may refer to not only producing a classification result of an object of interest but also detecting an area in which the object of interest is located in a given image.

The object recognition system may include an object recognition apparatus 100, a data source 200 which provides a training dataset, and a data source 300 which provides a recognition target image. However, this is merely an exemplary embodiment used to accomplish the objectives of the inventive concept, and some components can be added or removed if necessary.

The object recognition apparatus 100 is a computing device that trains an object recognition model based on weakly supervised learning using a training target image given classification results of objects of interest and recognizes an object of interest in a recognition target image using the trained object recognition model. Here, the weakly supervised learning refers to a machine learning method in which undesignated target information such as the location of an object of interest is learned using a training dataset given designated target information such as classification results of objects of interest. That is, the object recognition apparatus 100 can recognize the location of an object of interest through training even if information about the location of the object of interest is not included in a training dataset.

The computing device may be, e.g., a notebook computer, a desktop computer, or a laptop computer. However, the computing device is not limited to these examples and can be implemented as any device having a computing function.

The object recognition device 100 may obtain a training target image included in a training dataset from the data source 200 or a recognition target image from the data source 300. The object recognition apparatus 100 may obtain the training target image or the recognition target image through a network. However, the data sources 200 and 300 can also be located within the object recognition apparatus 100 depending on an implementation method.

The data source 200 is a repository which provides a training dataset. The training dataset includes a training target image given classification results of objects of interest. The training dataset may also include a training target image given the location information of objects of interest in addition to classification results of the objects of interest or a training target image not given classification results of objects of interest. The data source 200 may be implemented as, but not limited to, a database-based storage device.

A training target image 210b given classification results of objects of interest is an image having tag information 210a that indicates the classification results of the objects of interest. For example, in the medical field, the tag information 210a may include information about the presence or absence of a lesion or information about a pathological diagnosis result. The training target image 210b may be a radiographic image such as a two-dimensional (2D) X-ray image or a computed tomography (CT) image. For reference, the term "tag" can be used interchangeably with the terms "annotation" and "label" in the art to which the inventive concept pertains. However, it should be noted that these terms refer to the same concept.

The data source 300 is a repository which provides a recognition target image 310 without tag information. For example, in the medical field, the recognition target image 310 may be a radiographic image of a patient who needs to be pathologically diagnosed.

The object recognition system according to the inventive concept can be applied to various fields. For example, if applied to the medical field, the object recognition system may be a medical diagnosis system which learns a radiographic image given only a classification result such as information about the presence or absence of a lesion and predicts a pathological diagnosis result including the information about the presence or absence of the lesion and an area in which the lesion is located in a radiographic image of a patient.

Until now, the object recognition system according to the embodiment has been described with reference to FIG. 1. An object recognition apparatus 100 according to an embodiment will hereinafter be described.

Object Recognition Apparatus

As described above, the object recognition apparatus 100 is a computing device that trains an object recognition model using a training target image given classification results of objects of interest and recognizes an object of interest in a recognition target image using the object recognition model.

For better understanding, the result of object recognition performed on a recognition target image 320 using the object recognition apparatus 100 will first be described with reference to FIG. 2.

Figure 2:
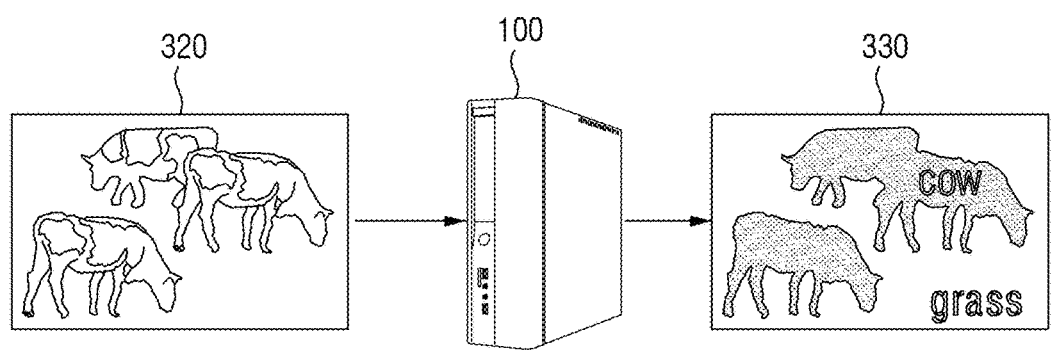
FIG. 2 illustrates an example of an input and an output of an object recognition apparatus.

Referring to FIG. 2, the object recognition apparatus 100 may recognize objects included in the recognition target image 320 using the trained object recognition model. For example, if the recognition target image 320 includes objects of interest such as 'cows' and 'grass,' the object recognition apparatus 100 may recognize not only classification results indicating that the 'cows' and the 'grass' exist in the recognition target image 320 but also areas in which the 'cows' and the 'grass' are located. Therefore, the object recognition apparatus 100 may convert the recognition target image 320 into an image 330 which is divided into the area of the 'cows' and the area of 'grass' and output the image 330.

The image 330 may be an image obtained by overlapping activation maps of the objects of interest included in the recognition target image 320 and presented in the form of a heat map.

The activation map, as used herein, denotes a feature map generated for each object of interest. In the art to which the inventive concept pertains, the activation map may also be called a class-specific activation map. However, it should be noted that both terms refer to the same concept.

Components and operation of the object recognition apparatus 100 will now be described with reference to FIGS. 3 and 4.

Figure 3:
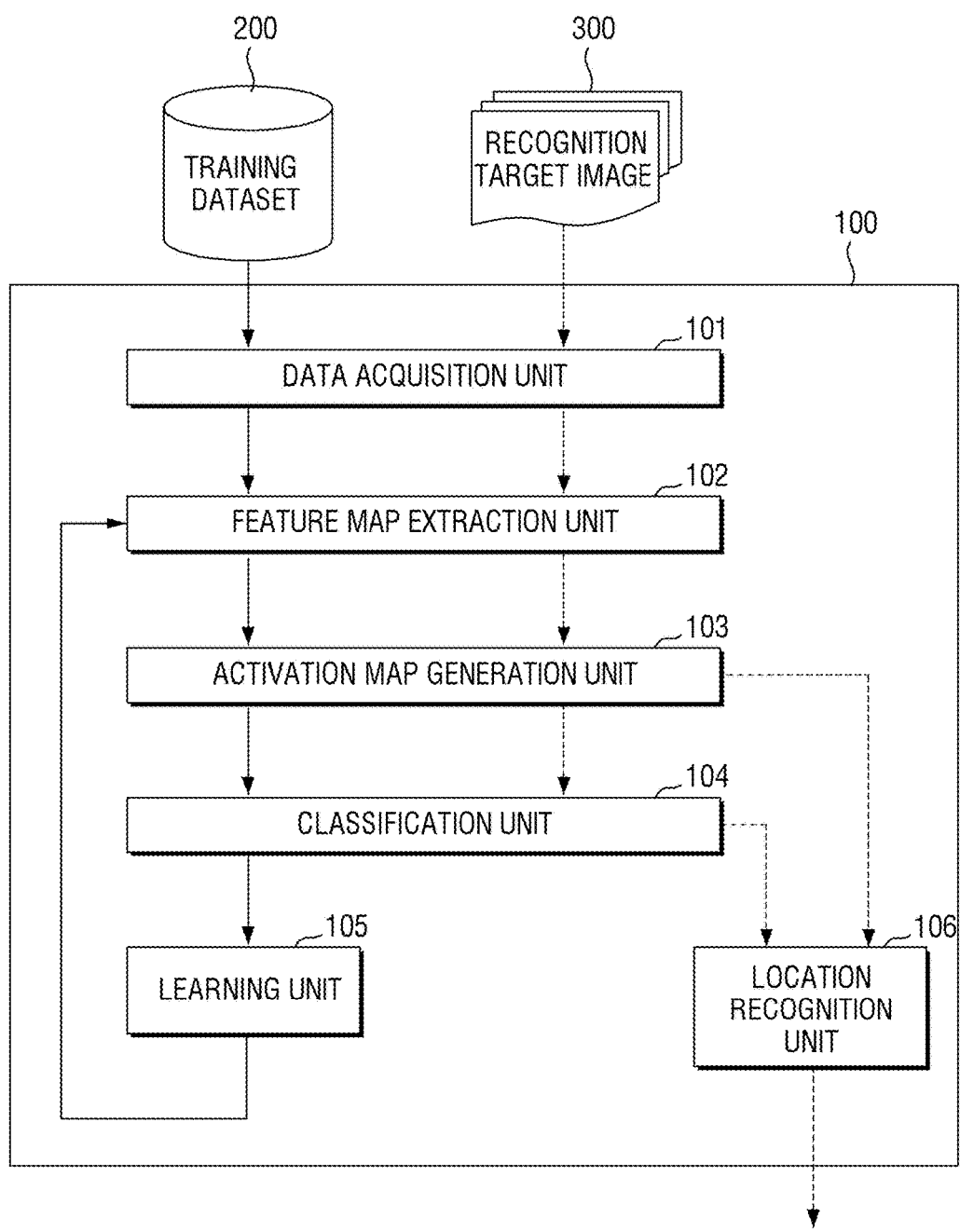
FIG. 3 is a functional block diagram of an object recognition apparatus according to an embodiment.

FIG. 3 is a functional block diagram of an object recognition apparatus 100 according to the inventive concept.

Referring to FIG. 3, the object recognition apparatus 100 may include a data acquisition unit 101, a feature map extraction unit 102, an activation map generation unit 103, a classification unit 104, a learning unit 105, and a location recognition unit 106. In FIG. 3, components only related to the embodiment of the inventive concept are illustrated. However, other general-purpose components can also be included in addition to the components illustrated in FIG. 3.

Specifically, the data acquisition unit 101 obtains data such as a training target image included in a training dataset and a recognition target image from data sources 200 and 300 provided inside or outside the object recognition apparatus 100. The data acquisition unit 101 may obtain data in various ways according to an implementation method. For example, if each of the data sources 200 and 300 is implemented as a database, the data acquisition unit 101 may obtain data using a query.

Using a preset number of filters, the feature map extraction unit 102 extracts feature maps showing various features of objects of interest from an image obtained by the data acquisition unit 101. For reference, the term "filter" can be used interchangeably with the term "kernel" in the art to which the inventive concept pertains, and the size and number of the filters may be preset.

For example, the feature map extraction unit 102 may extract a feature map related to the shape of objects and a feature map related to the color of the objects from an obtained image. A feature map extracted by the feature map extraction unit 102 may vary according to values of a weight matrix of a filter, and the values of the weight matrix may be adjusted to appropriate values by performing training using a training dataset. A method of extracting feature maps from a given image using the feature map extraction unit 102 will be described in detail later with reference to FIGS. 7 and 8.

The activation map generation unit 103 generates an activation map for each object of interest by accumulating a plurality of feature maps extracted from the feature map extraction unit 102. That is, a separate activation map may be generated for each object of interest. The difference between a feature map and an activation map lies in that the feature map includes features of all objects of interest included in a given image, whereas the activation map includes features of only one object. A method of generating an activation map for each object of interest using the activation map generation unit 103 will be described in detail later with reference to FIGS. 9 through 12.

The classification unit 104 outputs classification results of a given image using activation maps generated by the activation map generation unit 103. To this end, the classification unit 104 may calculate a representative value of each object of interest by aggregating activation values included in a corresponding activation map and determine classification results based on the representative values. Here, the representative value can be understood as a value into which a plurality of activation values included in an activation map are abstracted. A method of calculating the representative value will be described in detail later with reference to FIG. 13.

The learning unit 105 determines an error by comparing classification results output from the classification unit 104 with classification results given to a training target image and performs learning in a way that minimizes the error. For example, the learning unit 105 may adjust the values of the weight matrix of each filter of the feature map extraction unit 102 by back-propagating the error. The back-propagating is an algorithm widely known in the art to which the inventive concept pertains and thus will now be described in detail.

When a recognition target image is input and when an object of interest included in the recognition target image is determined by the classification unit 104, the location recognition unit 105 recognizes an area in which the determined object of interest is located in the recognition target image using an activation map of the determined object of interest.

Although not illustrated in FIG. 3, the object recognition apparatus 100 according to the inventive concept may further include a validation unit. The validation unit may validate a trained object recognition model using a test dataset. For example, the validation unit may validate the object recognition model using a k-fold cross validation technique. A method of validating the object recognition model using the validation unit will be described later with reference to FIG. 14.

Each component described above with reference to FIG. 3 may be implemented as a software component or a hardware component such as a field programmable gate array (FPGA) or application specific integrated circuit (ASIC). However, the components are not limited to the software or hardware components. A component may advantageously be configured to reside on the addressable storage medium and configured to execute on one or more processors. The functionality provided for in the components may be combined into fewer components or further separated into additional components.

Figure 4:
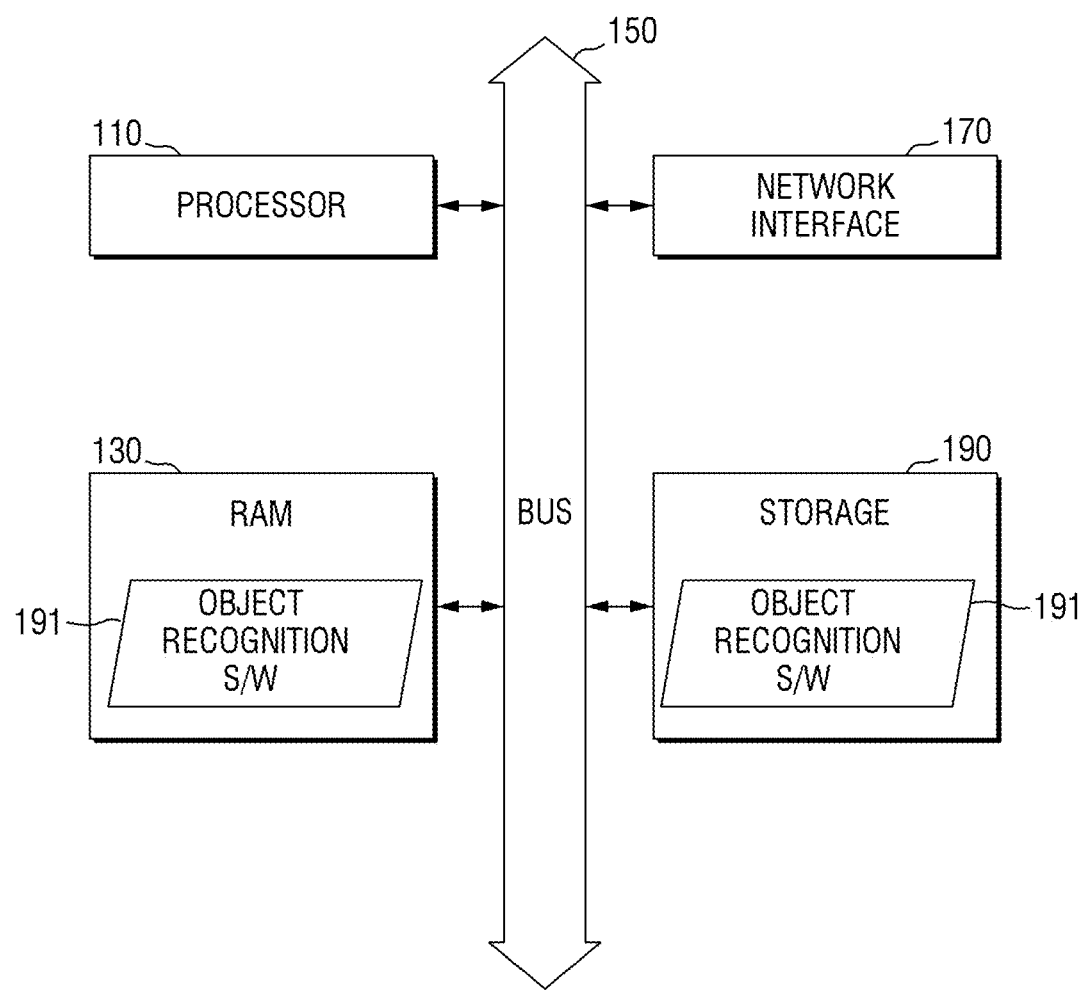
FIG. 4 illustrates the hardware configuration of an object recognition apparatus according to an embodiment.

FIG. 4 illustrates the hardware configuration of the object recognition apparatus 100.

Referring to FIG. 4, the object recognition apparatus 100 includes one or more processors 110, a bus 150, a network interface 170, a memory 130 which loads a computer program to be executed by the processors 110, and a storage 190 which stores object recognition software 191. In FIG. 4, components only related to the embodiment of the inventive concept are illustrated. Therefore, it will be understood by those of ordinary skill in the art that other general-purpose components can also be included in addition to the components illustrated in FIG. 4.

The processors 110 control the overall operation of each component of the object recognition apparatus 100. The processors 110 may include a central processing unit (CPU), a micro-processor unit (MPU), a micro-controller unit (MCU), or any form of processor well known in the art to which the inventive concept pertains. In addition, the processors 110 may perform an operation on at least one application or program for executing methods according to embodiments of the inventive concept. The object recognition apparatus 100 may include one or more processors.

The memory 130 stores various data, commands and/or information. To execute object recognition methods according to embodiments, the memory 130 may load one or more programs 191 from the storage 190. In FIG. 4, a random access memory (RAM) is illustrated as an example of the memory 130.

The bus 150 provides a communication function between the components of the object recognition apparatus 100. The bus 150 may be implemented as various forms of bus such as an address bus, a data bus and a control bus.

The network interface 170 supports wired and wireless Internet communication of the object recognition apparatus 100. In addition, the network interface 170 may support various communication methods as well as Internet communication. To this end, the network interface 170 may include various communication modules well known in the art to which the inventive concept pertains.

The network interface 170 may obtain data from one or more data sources 200 and 300 illustrated in FIG. 2 through a network.

The storage 190 may non-temporarily store one or more programs. In FIG. 4, the object recognition software 191 is illustrated as an example of the programs.

The storage 190 may include a nonvolatile memory such as a read only memory (ROM), an erasable programmable ROM (EPROM), an electrically erasable programmable ROM (EEPROM) or a flash memory, a hard disk, a removable disk, or any form of computer-readable recording medium well known in the art to which the inventive concept pertains.

The object recognition software 191 may perform an object recognition method based on weakly supervised learning.

More specifically, the object recognition software 191 may be loaded to the memory 130 and executed by the processors 110. The object recognition software 191 includes an operation of extracting a plurality of feature maps from a training target image given classification results of objects of interest, an operation of generating an activation map for each of the objects of interest by accumulating the feature maps, an operation of calculating a representative value of each of the objects of interest by aggregating activation values included in the activation map of the object of interest, an operation of determining an error by comparing classification results determined using the representative values of the objects of interest with the given classification results, and an operation of updating a convolutional neural network (CNN)-based object recognition model by back-propagating the error.

In addition, the object recognition software 191 may include an operation of training a CNN-based object recognition model using a training target image and an operation of recognizing an object of interest included in a recognition target image using the trained object recognition model. Here, the object recognition model includes a convolution layer which extracts a plurality of feature maps from the training target image and a deconvolution layer which increases the sizes of the feature maps. A weight matrix of each filter used in the deconvolution layer may be a matrix obtained by transposing a weight matrix of each filter used in the convolution layer corresponding to the deconvolution layer.

Until now, the configuration and operation of the object recognition apparatus 100 according to the embodiment have been described with reference to FIGS. 3 and 4. An object recognition model referred to in some embodiments will hereinafter be described.

Object Recognition Model

An object recognition model is a model that outputs classification results indicating the types of objects of interest included in an input image and generates an activation map showing an area in which each of the objects of interest is located in the image. Even when location information of each object of interest is not included in a training dataset, the object recognition model can accurately output an area in which each object of interest is located in an input image through training based on weakly supervised learning.

The object recognition model will now be described with reference to FIG. 5.

Figure 5:
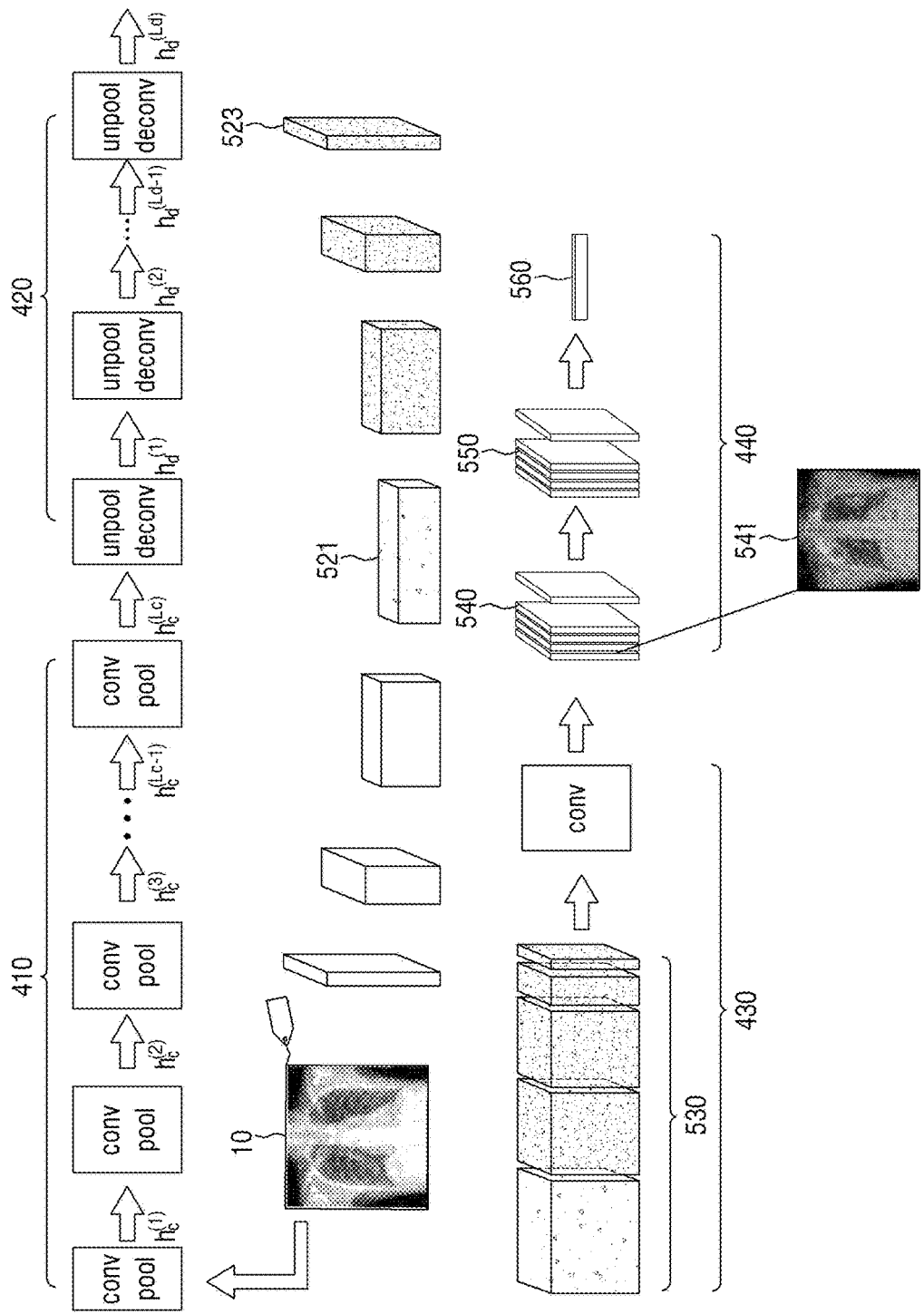
FIG. 5 illustrates an example object recognition model which can be referred to in some embodiments.

FIG. 5 illustrates an example object recognition model. In FIG. 5, each three-dimensional (3D) quadrilateral (521, 523, 530, 540 or 550) represents feature maps or activation maps output from each layer. In addition, the area of the 3D quadrilateral represents the size of the feature maps or the activation maps, and the depth of the 3D quadrilateral represents the number of the feature maps or the activation maps.

Referring to FIG. 5, the object recognition model may be based on a CNN and include a plurality of convolution layers 410 and a plurality of deconvolution layers 420. In addition, the object recognition model may further include a first output layer 430 which outputs an activation map for each object of interest and a second output layer 440 which outputs classification results of an input image based on the activation maps.

For reference, the term "deconvolution layer" can be used interchangeably with the term "transposed convolution layer." However, it should be noted that both terms refer to the same object.

Specifically, each of the convolution layers 410 extract a plurality of feature maps from an input training target image 210 or an input recognition target image through a convolution operation. The number of feature maps extracted by each of the convolution layers 410 may vary according to the number of filters used in each of the convolution layers 410. The feature maps may become smaller or include more abstracted features as they pass through a plurality of convolution layers. Here, abstraction may refer to a task of extracting core data from a plurality of pieces of data, and the abstracted features may refer to core features.

Each of the convolution layers 410 may include a pooling layer. The pooling layer reduces the sizes of input feature maps through a pooling operation that performs sub-sampling, thereby reducing the complexity of the object recognition model and preventing overfitting. The sub-sampling may be performed in various ways according to an implementation method, such as average sampling and max sampling. If the max sampling method is used, noise having a small feature value is removed as it passes through each pooling layer. Therefore, core features can be better extracted. The convolution operation and the pooling operation will be described in detail later with reference to FIG. 8.

Each of the deconvolution layers 420 increases the sizes of a plurality of feature maps while maintaining a pattern shown in the feature maps by performing a convolution operation. Here, increasing the sizes of the feature maps may be to restore the sizes of the feature maps to the sizes of the feature maps input to a corresponding convolution layer.

A weight matrix of each filter used in each of the deconvolution layers 410 may be a matrix obtained by transposing a weight matrix of each filter used in a corresponding convolution layer. That is, according to the inventive concept, tied weight matrix values are set for filters of a convolution layer and filters of a deconvolution layer corresponding to the convolution layer. Therefore, the complexity of the object recognition model can be reduced, and the object recognition model can be trained more efficiently. In addition, according to experimental results of the inventive concept, the use of the tied weight matrix improves the accuracy of recognizing the location of an object of interest.

Each of the deconvolution layers 420 may include an unpooling layer. The unpooling layer increases the sizes of feature maps by performing an unpooling operation which is opposite to the pooling operation. The unpooling operation will be described in detail later with reference to FIG. 8.

The reason why each of the deconvolution layers 420 includes an unpooling layer corresponding to a pooling layer is as follows. While the pooling layer can extract feature values indicating core features in a feature map, location information of each feature value indicating the core feature is lost from the feature map. Here, the loss of the location information of each feature value is a factor that reduces the accuracy of recognizing the location of an object of interest. To compensate for this drawback, the unpooling layer is included in each of the deconvolution layers 420.

That is, the object recognition model of the inventive concept includes a pooling layer which extracts feature values indicating core features and an unpooling layer which increases the sizes of feature maps to restore location information of each feature value indicating the core feature. Therefore, an area in which each object of interest is located in a given image can be output accurately.

The first output layer 430 accumulates a plurality of feature maps extracted by the convolution layers 410 and the deconvolution layers 420 and outputs an activation map 540 for each object of interest through a convolution operation. Here, the first output layer 430 accumulates a plurality of feature maps to generate the activation map 540 more accurately by aggregating various features shown in the feature maps.

The first output layer 430 may generate the activation map 540 by accumulating at least two of feature maps ranging from feature maps 521 input to a first deconvolution layer to feature maps 523 output from a last deconvolution layer. Noise is removed from feature maps as the feature maps pass through the convolution layers 410. Accordingly, the feature maps output from the convolution layers 410 include core features. If the activation map 540 is generated by accumulating some of these feature maps, the generated activation map 540 may more accurately show a feature area indicating an object of interest. The number of feature maps accumulated and feature maps selected to be accumulated may vary according to an implementation method.

For reference, feature maps 530 shown in FIG. 5 are an accumulation of the feature maps 521 input to the first deconvolution layer and all feature maps output from the deconvolution layers 420. An image 541 shown in FIG. 5 is an activation map which is generated using a radiographic image and presented in the form of a heat map.

The second output layer 440 calculates a representative value of each object of interest using the activation map 540 and outputs classification results 560 of the objects of interest in the input image based on the calculated representative values. For example, if the number of the objects of interest is K, the second output layer 440 may calculate K representative values. If an activation map for the background is generated depending on an implementation method, (K+1) representative values may be calculated.

Since the object recognition model includes the second output layer 440, it can be trained based on weakly supervised learning. That is, since classification results of objects of interest are output from the second output layer 440, the object recognition model can be trained by comparing the output classification results with classification results of the objects of interest included in a training dataset.

The training may be performed by, e.g., the object recognition apparatus 100. Specifically, the object recognition model may be trained by back-propagating an error determined based on the above comparison. As the object recognition model is trained, a weight value of each filter used in each layer 410, 420 or 430 is adjusted, and the adjustment of the weight value increases the accuracy of the activation map 540 indicating an area in which an object of interest is located in a given image.

Until now, the object recognition model which can be referred to in some embodiments has been described. An object recognition method according to an embodiment will hereinafter be described.

Object Recognition Method

An object recognition method according to an embodiment can be performed by any computing device. However, for ease of description, it is assumed that each operation of the object recognition method is performed by the object recognition apparatus 100. The subject that performs each operation of the object recognition method may sometimes be omitted for ease of description.

In addition, each operation of the object recognition method may be an operation performed by the object recognition apparatus 100 as the object recognition software 191 is executed by the processors 110. The object recognition method to be described below is merely an exemplary embodiment used to accomplish the objectives of the inventive concept, and some operations can be added or removed if necessary.

The object recognition method according to the inventive concept may largely include an operation of training an object recognition model using a training target image given classification results of objects of interest and an operation of recognizing an object of interest included in a recognition target image using the trained object recognition model.

The operation of training the object recognition model will now be described in detail with reference to FIGS. 6 through 13.

Object Recognition Method—Training

Figure 6:
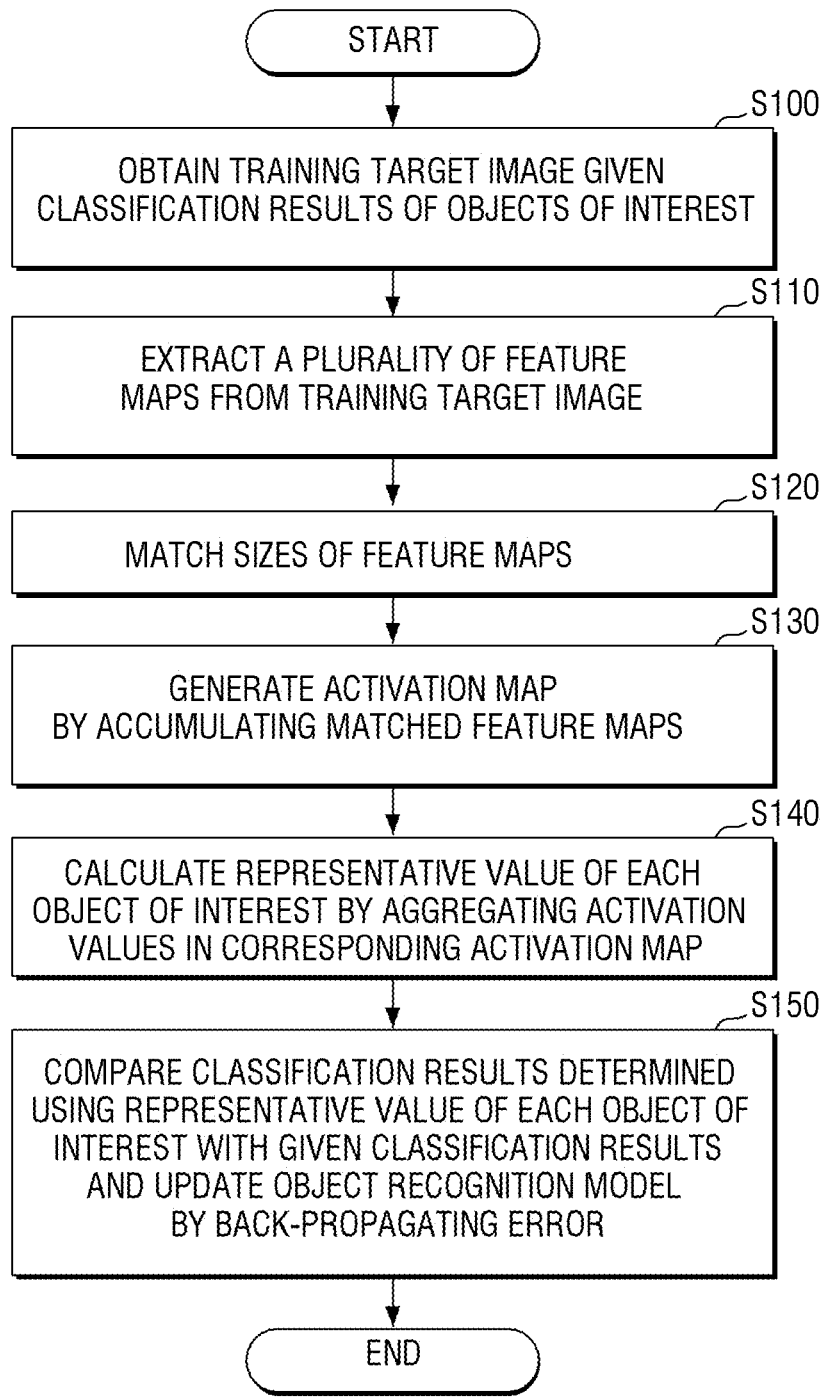
FIG. 6 is a flowchart illustrating an operation of training an object recognition model, which can be referred to in some embodiments.

FIG. 6 is a flowchart illustrating an operation of training an object recognition model.

Referring to FIG. 6, the object recognition apparatus 100 obtains a training target image given classification results of objects to be recognized (operation S100). As described above, the classification results of the objects of interest may refer to information about the presence or absence of the objects of interest or information about, e.g., the types of the objects of interest included in the training target image.

Next, the object recognition apparatus 100 extracts a plurality of feature maps from the training target image (operation S110). The feature maps may be output from convolution layers or deconvolution layers and may later be used to generate an activation map in operation S130. As described above, the feature maps may be composed of all or some of feature maps input to a first deconvolution layer and feature maps output from each deconvolution layer. The operation of extracting the feature maps (operation S110) will be described in detail later with reference to FIG. 7.

The object recognition apparatus 100 matches the sizes of the feature maps (operation S120). Since the sizes of the feature maps are increased by an unpooling operation and a convolution operation in the deconvolution layers, the feature maps output from the deconvolution layers may have different sizes. Therefore, it is required to match the size of each feature map before generating an activation map.

For example, the object recognition apparatus 100 may match the sizes of the feature maps based on a largest feature map. However, a feature map based on which the sizes of the feature maps are matched may vary according to an implementation method.

Next, the object recognition apparatus 100 generates an activation map for each object of interest by accumulating the matched feature maps (operation S130). That is, the object recognition apparatus 100 generates an activation map showing features of each predefined object of interest.

The operation of generating the activation map (operation S130) will be described in detail later with reference to FIGS. 11 and 12.

Next, the object recognition apparatus 100 calculates a representative value of each object of interest by aggregating activation values included in the activation map (operation S140). As described above, the representative value is a value obtained by aggregating and abstracting activation values included in each activation map. The representative value can be understood as a value indicating how many features of an object of interest have been extracted from a given image. That is, it can be understood that the greater the representative value, the higher the probability that an object of interest will exist in a given image.

A method of calculating the representative value may vary according to an implementation method. For example, the representative value may be determined to be a maximum value or an average value of activation values included in an activation map. However, the representative value may preferably be determined through a Log-Sum-Exp (LSE) operation. This is because the same weight is assigned to all activation values included in an activation map when the maximum value or the average value is determined to be the representative value, and assigning the same weight can reduce the accuracy of the representative value indicating the probability that an object of interest will exist. The operation of calculating the representative value (operation S140) will be described in detail later with reference to FIG. 13.

Finally, the object recognition apparatus 100 determines classification results of the training target image based on the representative value of each object of interest and determines an error by comparing the determined classification results with the given classification results. In addition, the object recognition apparatus 100 updates the object recognition model by back-propagating the determined error (operation S150). Specifically, the object recognition model may be updated by adjusting a filter value of each layer by back-propagating the error in such a way that minimizes an error value calculated through a cost function. The cost function may be, for example, a cross entropy function. The cross entropy function is a technology widely known in the art to which the inventive concept pertains, and thus a description of the cross entropy function is omitted.

For reference, a drop-out technique may be applied to prevent overfitting in the operation of training the object recognition model. The drop-out technique is a technique of updating a filter of a neural network node based on a preset probability. The drop-out technique is a technique widely known in the art to which the inventive concept pertains, and thus a description of the drop-out technique is omitted.

Until now, the operation of training the object recognition model using the object recognition apparatus 100 has been described with reference to FIG. 6. For rapid processing, this operation may be performed in parallel by a plurality of processors or may be performed in a distributed manner by a plurality of object recognition apparatuses 100.

For better understanding, each sub-operation of the training operation will now be described with reference to FIGS. 7 through 13.

First, the operation of extracting the feature maps (operation S110) will be described with reference to FIGS. 7 and 8.

As described above, the object recognition apparatus 100 extracts a plurality of feature maps using a plurality of convolution layers and a plurality of deconvolution layers. For example, the object recognition apparatus 100 may extract a plurality of feature maps in the sequence illustrated in FIG. 7. For ease of description, it is assumed that two convolution layers and two deconvolution layers are provided.

Figure 7:
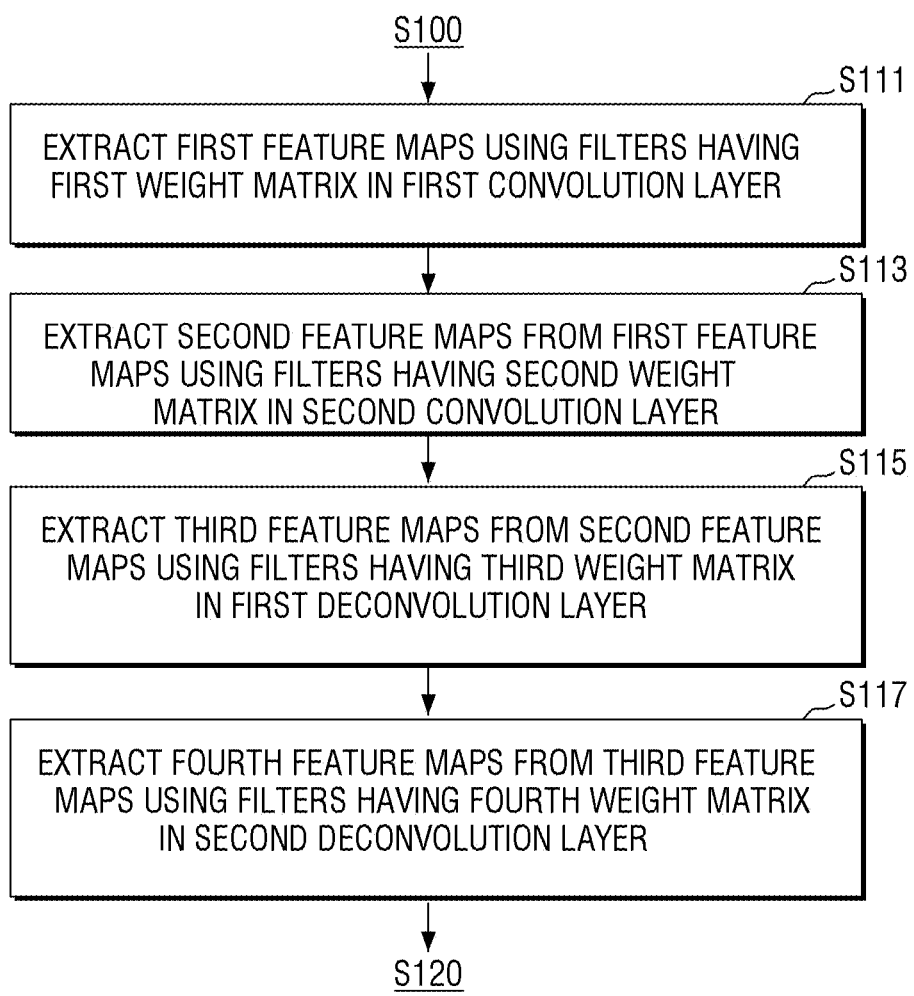
FIG. 7 is a detailed flowchart illustrating an operation of extracting feature maps included in the operation of FIG. 6.

Referring to FIG. 7, the object recognition apparatus 100 extracts first feature maps using filters having a first weight matrix in a first convolution layer (operation S111). Specifically, the first feature maps may be extracted by performing a convolution operation on an image input to the first convolution layer and the weight matrix of each filter. Here, the size and number of the filters may be preset, and the weight of each filter may be given an initial value according to a preset standard and then adjusted as the training operation proceeds. The number of the first feature maps extracted may be equal to the number of the filters.

In addition, although not illustrated in the flowchart of FIG. 7, each convolution layer may perform a pooling operation for removing noise through sub-sampling and reducing the sizes of the feature maps, and feature values of each feature map may be calculated using an activation function. The activation function may be, for example, a rectified linear unit (ReLU) function. For reference, to solve a vanishing gradient problem in which learning through back-propagation is not performed properly as the number of layers increases, the ReLU function instead of a sigmoid function may be used as an activation function. The ReLU function is an activation function well known in the art to which the inventive concept pertains, and thus a description of the ReLU function is omitted. The convolution operation and the pooling operation performed by each convolution layer will be described in detail later with reference to FIG. 8.

Next, the object recognition apparatus 100 extracts second feature maps from the first feature maps using filters having a second weight matrix in a second convolution layer (operation S113). The second feature maps may include more abstracted features than the first feature maps and are extracted in the same way as in operation S111.

The process of extracting feature maps through a convolution layer may be generalized as in Equation (1). In other words, the object recognition apparatus 100 may extract each feature map through each convolution layer using Equation (1) below. In Equation (1), $h_c^{(i)}$ indicates a feature map extracted by an $i^{th}$ convolution layer, σ indicates an activation function, an operator * indicates a convolution operation, and $W_c^{(i)}$ indicates a weight of a filter used in the $i^{th}$ convolution layer. In addition, $b_c^{(i)}$ indicates a bias given in the $i^{th}$ convolution layer.

$$h_c^{(i)} = \sigma(h_c^{(i-1)} * W_c^{(i)} + b_c^{(i)}) \qquad (1)$$

The object recognition apparatus 100 increases the sizes of the second feature maps extracted by the last convolution layer through the deconvolution layers. The deconvolution layers are used here to increase the sizes of the feature maps while maintaining a pattern shown in the feature maps, so that an area in which features of each object of interest are detected in a recognition target image can be determined more accurately.

More specifically, an area in which an object of interest is located in a given image can be recognized more accurately using both a pooling layer included in each convolution layer and an unpooling layer included in each deconvolution layer. According to experimental results of the inventive concept, a false positive (FP) error in which an area in which an object of interest is not located is detected is noticeably reduced.

As for outputting feature maps through the deconvolution layers, the object recognition apparatus 100 outputs third feature maps from the second feature maps using filters having a third weight matrix in a first deconvolution layer (operation S115). Specifically, the second feature maps extracted by the last convolution layer are input to the first deconvolution layer, and the third feature maps are output through a convolution operation performed on the second feature maps and the third weight matrix.

In addition, although not illustrated in the flowchart of FIG. 7, an unpooling operation for increasing the sizes of the feature maps may be performed in each deconvolution layer, and feature values of each feature map may be calculated through an activation function. Here, the activation function may also be the ReLU function as in the convolution layers. The unpooling operation will be described in detail later with reference to FIG. 8.

Next, the object recognition apparatus 100 outputs fourth feature maps from the third feature maps using filters having a fourth weight matrix in a second deconvolution layer (operation S117). The fourth feature maps are output in the same way as in operation S115.

The process of extracting feature maps through a deconvolution layer may be generalized as in Equation (2). In Equation (2), $h_d^{(j)}$ indicates a feature map extracted by a $j^{th}$ deconvolution layer, σ indicates an activation function, an operator * indicates a convolution operation, and $W_d^{(j)}$ indicates a weight of a filter used in the $j^{th}$ convolution layer. In addition, $b_d^{(j)}$ indicates a bias given in the $j^{th}$ deconvolution layer.

$$h_d^{(j)} = \sigma(h_d^{(j-1)} * W_d^{(j)} + b_d^{(j)}) \quad (2)$$

As shown in Equation (2), the operation performed in a deconvolution layer is also a convolution operation. However, to make a weight of a filter learned efficiently, a weight of each filter used in the deconvolution layer may use a matrix obtained by transposing a weight matrix of each filter used in a corresponding convolution layer. That is, the third weight matrix used in the first deconvolution layer may be a matrix obtained by transposing the second weight matrix of the second convolution layer corresponding to the first deconvolution layer, and the fourth weight matrix used in the second deconvolution layer may be a matrix obtained by transposing the first weight matrix.

If this is generalized, the weight $W_d^{(j)}$ of a filter used in a deconvolution layer may be determined by Equation (3). In Equation (3) below, $L_c$ indicates the number of convolution layers.

$$W_d^{(j)} = W_c^{(L_c+1-j)T} \quad (3).$$

In summary, a convolution layer and a deconvolution layer may symmetrically correspond to each other, and a weight matrix of each filter used in the deconvolution layer may be a matrix obtained by transposing a weight matrix of each filter used in the corresponding convolution layer. In this way, the object recognition apparatus 100 may give tied weights to corresponding filters, thereby reducing the complexity of the object recognition model and performing learning more efficiently.

For better understanding, convolution and deconvolution operations and pooling and unpooling operations will now be described briefly with reference to FIG. 8.

FIG. 8 illustrates the concept of the above operations. Specifically, FIG. 8A illustrates a convolution operation, FIG. 8B illustrates a pooling operation, FIG. 8C illustrates a convolution operation performed in a deconvolution layer, and FIG. 8D illustrates an unpooling operation.

The convolution operation illustrated in FIG. 8A can be understood as an operation of extracting features of an object of interest from an image area having the same size as a filter size by using a filter. Referring to FIG. 8A, feature values in an image area having the same size as a filter size are extracted as one feature value. Therefore, a feature map may become smaller as the convolution operation proceeds. Depending on an implementation method, if a stride having a small value is used and if edges of the feature map are zero-padded, the size of the feature map may be reduced only through a pooling operation. Here, the stride denotes the number of pixels that are skipped when convolution is performed on an image or a feature map.

On the contrary, the convolution operation illustrated in FIG. 8C is an operation of increasing the size of the feature map extracted through the convolution operation of FIG. 8A while maintaining a pattern in the feature map. Referring to FIG. 8C, one feature value is converted into a plurality of feature values through the convolution operation.

The pooling operation illustrated in FIG. 8B is an operation of removing noise and reducing the size of a feature map through sub-sampling. A feature map shown on a lower right side of FIG. 8B is a feature map reduced in size by the pooling operation. In addition, an image shown on an upper right side of FIG. 8B stores location information of a value sampled to restore location information through an unpooling operation.

For reference, various sampling techniques such as average sampling and max sampling can be used for the pooling operation. However, max sampling for sampling a maximum value may be used to extract only differentiated features.

The unpooling operation illustrated in FIG. 8D is an operation of increasing the size of a feature map based on location information stored in a pooling process. Specifically, location information of a value sampled through a pooling operation may be restored by placing the sampled value at a location before the pooling operation, and the other values may be set to zero. In this way, the unpooling operation may be performed.

Until now, the operation of extracting the feature maps (operation S110) has been described with reference to FIGS. 7 and 8. The operation of matching the sizes of the feature maps will now be described with reference to FIGS. 9 and 10.

Figure 9:
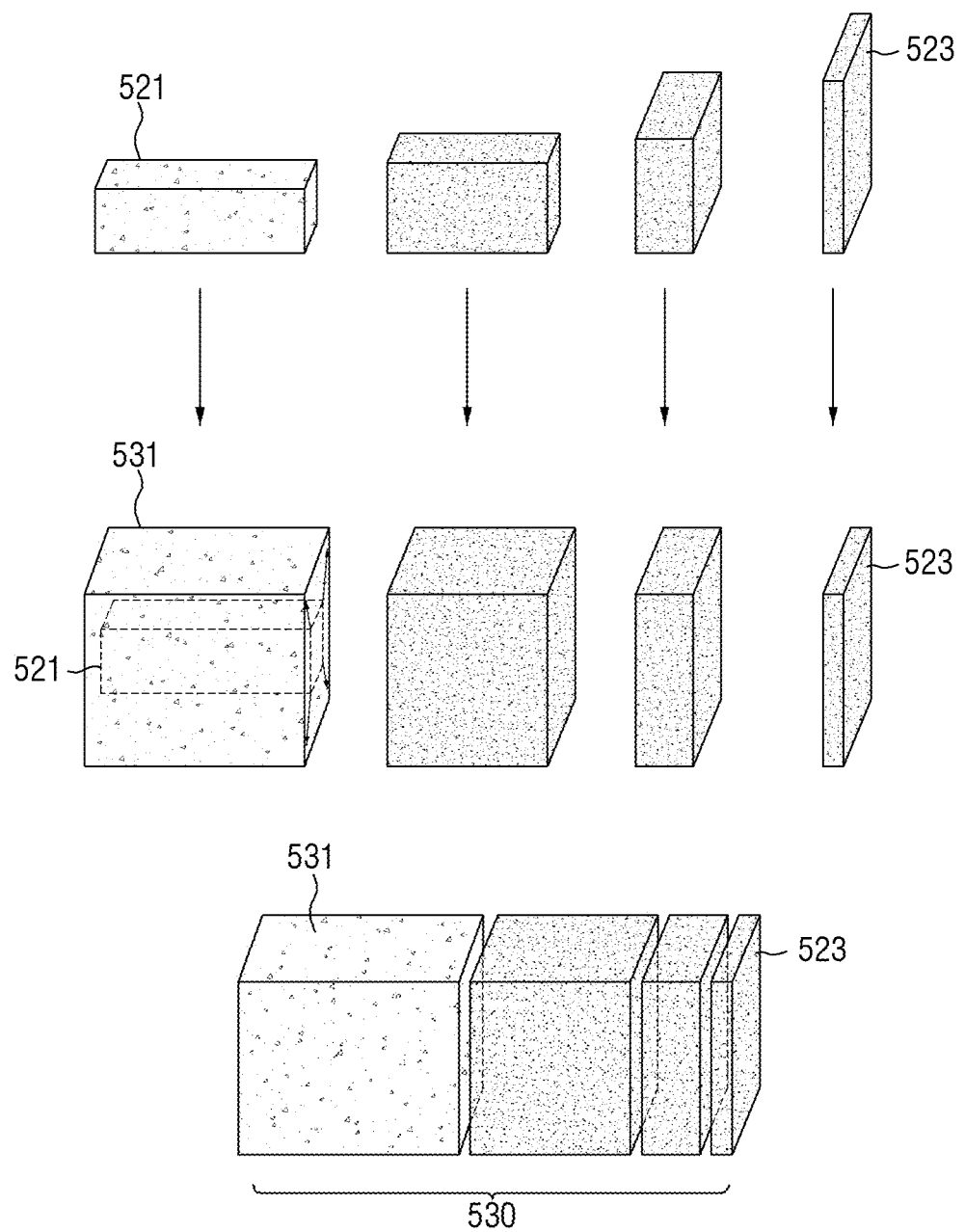
FIGS. 9 and 10 illustrate an operation of matching sizes of the feature maps included in the operation of FIG. 6.

FIG. 9 illustrates an example of the operation of matching the sizes of the feature maps (operation S120). In FIG. 9, quadrilaterals 521 and 531 shown in three dimensions represent a plurality of feature maps.

As described above, the object recognition apparatus 100 matches the sizes of a plurality of feature maps to generate an activation map by accumulating the feature maps. Here, the feature maps accumulated may be composed of all or some of feature maps extracted by a last convolution layer and feature maps successively output from deconvolution layers based on the feature maps extracted by the last convolution layer. In addition, the number of feature maps accumulated and feature maps selected to be accumulated may vary according to an implementation method. For reference, the feature maps extracted by the last convolution layer may be the same as feature maps input to a first deconvolution layer.

Referring to FIG. 9, the object recognition apparatus 100 may match the sizes of a plurality of feature maps based on the size of a preset feature map. For example, the object recognition apparatus 100 may match the sizes of a plurality of feature maps based on a largest feature map. That is, if all feature maps output from the deconvolution layers are accumulated, the object recognition apparatus 100 may increase the sizes of feature maps 521 based on the sizes of feature maps 523 output from a last deconvolution layer.

Specifically, the object recognition apparatus 100 may convert the feature maps 521 into feature maps 531 by increasing the sizes of the feature maps 521 and accumulate a plurality of enlarged feature maps as illustrated at the bottom of FIG. 9. The accumulated feature maps may have the same size but different abstraction levels. Therefore, an activation map for each object of interest can be generated more accurately based on abundant features.

Figure 10:
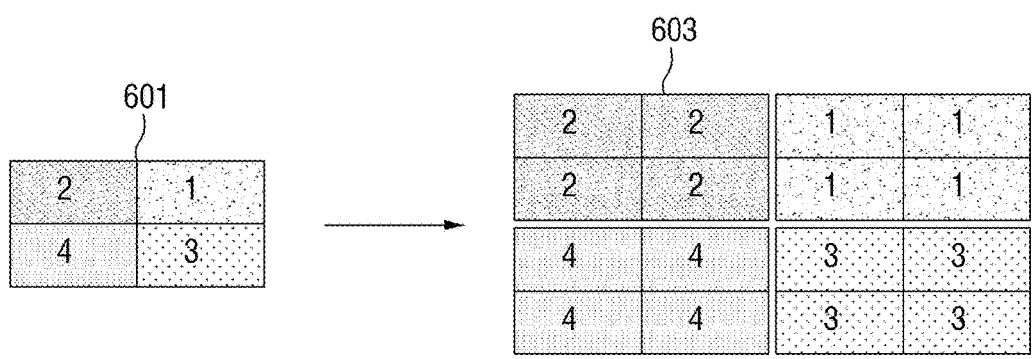

A method of increasing the size of a feature map may vary according to an implementation method. For example, referring to FIG. 10, the size of a feature map may be increased by copying each feature value included in the feature map to an enlarged area of the feature map. In FIG. 10, a 2×2 feature map 601 is enlarged to a 4×4 feature map 603. It should be noted that the example illustrated in FIG. 10 is merely an example of the method of increasing the size of a feature map.

Until now, the operation of matching the sizes of the feature maps (operation S120) has been described with reference to FIGS. 9 and 10. The operation of generating the activation map (operation S130) will now be described with reference to FIGS. 11 and 12.

The object recognition apparatus 100 may generate an activation map using Equation (4) below. In Equation (4), $h_m$ indicates an activation map, and $f^{(L_d)}$ indicates a plurality of feature maps whose sizes have been matched. In addition, an operator * indicates a convolution operation, $W_m$ indicates a weight of a filter, $b_m$ indicates a bias, and K indicates the number of activation maps. Lastly, R indicates a set of activation maps. For example, in the case of binary classification in which a classification result is produced based on the presence or absence of an object of interest, K may have a value of 2. In the case of multi-label classification based on the type of an object of interest, K may have a value obtained by adding 1 to a predefined number of objects of interest in view of an activation map representing the background.

$$h_m = f^{(L_d)} * W_m + b_m \in R^{K \times H^L_d \times W^L_d} \quad (4)$$

Figure 11:
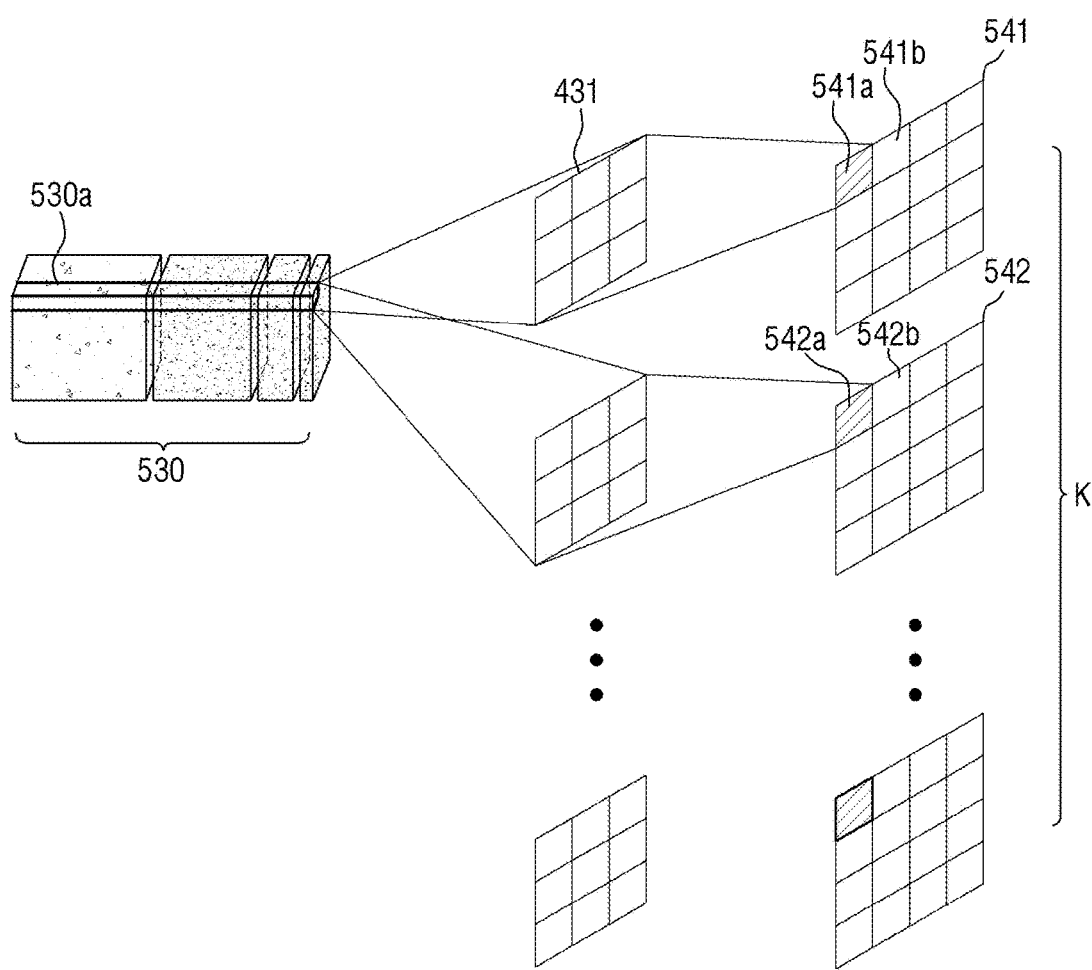
FIGS. 11 and 12 illustrate an operation of generating an activation map included in the operation of FIG. 6.

For better understanding, referring to FIG. 11, the object recognition apparatus 100 extracts K activation maps (541, 542, etc.) using K filters (431, etc). Here, a convolution operation may be performed on feature values assigned to the same location in a plurality of feature maps 530, as illustrated in FIG. 11. That is, to extract core features of an object of interest among features shown in the feature maps 530, the convolution operation should be performed on feature values at the same location in the feature maps 530.

Specifically, an activation value 541a at a first location in an activation map 541 is determined using feature values 530a at the first location in the feature maps 530, and an activation value 541b at a second location in the activation map 541 is determined using feature values at the second location in the feature maps 530. In addition, an activation value 542a at the first location in an activation map 542 is determined using the feature values 530a at the first location in the feature maps 530, and an activation value 542b at the second location in the activation map 542 is determined using the feature values at the second location in the feature maps 530.

For reference, in FIG. 11, the feature values 530a at the first location are illustrated as feature values assigned to a 1×1 area in the feature maps 530. However, this is merely an example used for ease of description, and the feature values 530a at the first location may also be feature values assigned to an area of n×n size (where n is a natural number of 2 or more).

In addition, to amplify the difference between activation values included in activation maps, a softmax operation may additionally be performed on activation values at the same location in the K activation maps. The difference between the activation values is amplified to prevent an FP error, in which features of an object of interest are shown in an area in which the object of interest is not located, by reinforcing core features and suppressing non-core features. However, the softmax operation is merely an example used to amplify the difference between activation values, and other operations can also be performed according to an implementation method.

Figure 12:
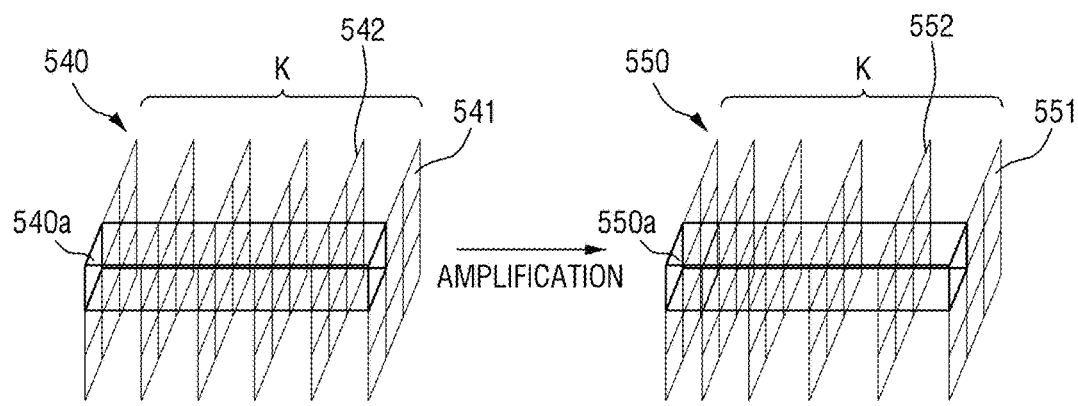

Referring to FIG. 12, a softmatx operation may be performed on values assigned to the same location in K activation maps 540. After the softmax operation, a relative difference between activation values 550a at a first location in the K activation maps 550 may become greater than a relative difference between activation values 540a at the first location in the K activation maps 540 before the softmax operation.

Until now, the operation of generating the activation map (operation S120) has been described with reference to FIGS. 11 and 12. As described above, various feature maps output from deconvolution layers are accumulated to generate an activation map that accurately shows an area in which an object of interest is located, and the area in which the object of interest is located is recognized using the activation map. Accordingly, the accuracy of object recognition can be improved.

The operation of calculating the representative value of each object of interest (operation S140) will now be described with reference to FIG. 13.

Figure 13:
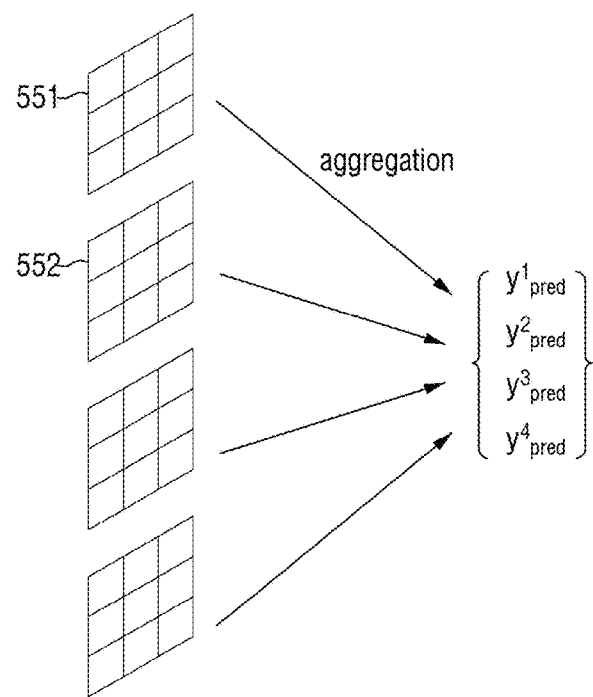
FIG. 13 illustrates an operation of calculating a representative value of each object of interest included in the operation of FIG. 6.

FIG. 13 illustrates an example of calculating a representative value of each object of interest by aggregating activation values included in a corresponding activation map. For ease of description, it is assumed that K has a value of 4.

Referring to FIG. 13, values $y^1_{pred}$, $y^2_{pred}$, $y^3_{pred}$ and $y^4_{pred}$ shown on the right are respective representative values of objects of interest. That is, the object recognition apparatus 100 calculates a representative value of an object of interest by aggregating activation values included in each activation map. Specifically, the object recognition apparatus 100 calculates a representative value $y^1_{pred}$ of a first object of interest by aggregating activation values included in an activation map 551 of the first object of interest and calculates a representative value $y^2_{pred}$ of a second object of interest by aggregating activation values included in an activation map 552 of the second object of interest.

A method of calculating a representative value may vary according to an implementation method. For example, the object recognition apparatus 100 may calculate the above representative values using Equation (5) below. Equation (5) is an equation for calculating a representative value using an LSE operation. In Equation (5), $\sigma(h_m)$ indicates an activation map 551 or 552 extracted through a softmax operation, c indicates the type of an object of interest, $y^c_{pre}$ indicates a representative value of an object of interest corresponding to the type c, and s indicates a control parameter. The control parameter s can be understood as a value for controlling a representative value calculation policy of the LSE operation by controlling a weight given to each activation value included in an activation map. As the value of s is smaller, the same weight may be given to each activation value. Therefore, an average activation value may be calculated as a representative value. On the contrary, as the value of s is greater, a different weight may be given to each activation value. Therefore, a large activation value may be calculated as the representative value. For reference, if K is 2, an ReLU function instead of the softmax operation may be used as σ.

$$y_{pred}^c = \frac{1}{s}\log\left(\frac{\sum_{i,j}\exp(s \cdot \sigma(h_m)_{i,j}^c)}{H^{L_d}W^{L_d}}\right). \quad (5)$$

A representative value of an object of interest implies information about how many features of the object of interest are shown in a given image or information about the probability that the object of interest will exist in the given image. Therefore, the object recognition apparatus 100 may determine classification results of objects of interest included in a given image using representative values. In addition, the object recognition apparatus 100 may determine an error by comparing the classification results of the objects of interest with given classification results and update an object recognition model by back-propagating the error. As described above, a cross entropy function may be used as a cost function to calculate an error, and a weight value of each filter may be adjusted by back-propagating the error in such a way that minimizes the cost function.

According to an embodiment, a pre-trained filter may be applied to some or all of layers that form an object recognition model. That is, the object recognition apparatus 100 may apply a filter trained to extract general features of objects from a given image, thereby reducing the time required to train the object recognition model and the cost of computing.

Until now, the operation of training the object recognition model using the object recognition apparatus 100 has been described in detail with reference to FIGS. 6 through 13. As described above, the object recognition apparatus 100 may train an object recognition model using a training target image given classification results of objects of interest, and the trained object recognition model may not only output classification results of a given image but also accurately recognize an area in which a particular object is located in the given image.

An operation of validating the trained object recognition model will now be described briefly.

Object Recognition Method—Validation

The object recognition apparatus 100 may validate an object recognition model after the training operation or during the training operation. The object recognition model may be validated using various validation methods. For example, the object recognition apparatus 100 may validate the object recognition model using a k-fold cross validation technique. A method of validating the object recognition module using the object recognition apparatus 100 will now be described with reference to FIGS. 14A through 14C.

FIG. 14A illustrates the concept of a k-fold cross validation technique.

Referring to FIG. 14A, the object recognition apparatus 100 may divide an original training dataset into k datasets, train an object recognition model using (k−1) datasets, validate the object recognition model using the other one dataset as a test dataset, and calculate average error or average accuracy by performing validation a total of k times by changing the test dataset.

Depending on an implementation method, if the calculated average error or average accuracy does not meet a preset standard, the object recognition apparatus 100 may change parameters of the object recognition model and retrain the object recognition model, thereby generating a new object recognition model. Alternatively, the object recognition model may be reconstructed using a pre-trained model such as VGG16 or VGG19. Here, the parameters of the object recognition model may be, for example, the size and number of filters, a stride, the number of convolution layers, the number of deconvolution layers, etc.

Alternatively, depending on an implementation method, the object recognition apparatus 100 may establish a plurality of different candidate object recognition models and cross-validate each model. Then, the object recognition apparatus 100 may determine a candidate object recognition model having a highest average accuracy value as an object recognition model to be used in the object recognition operation. For reference, to increase the accuracy of recognition, the object recognition apparatus 100 may determine a plurality of object recognition models, combine the object recognition models using various ensemble techniques, and use the combination result in object recognition.

To evaluate the accuracy of an object recognition model, the object recognition apparatus 100 may use at least one evaluation metric selected from precision, recall, and F-Measure. For example, if reducing FP is more important, the precision may be used as an evaluation metric. If reducing false negative (FN) is important, the recall may be used as an evaluation metric. Alternatively, an appropriate F-Measure such as $F_2$ or $F_{0.5}$ may be used according to an implementation method. Equations used to calculate the precision, the recall, and the F-Measure are widely known in the art to which the inventive concept pertains, and thus a description of the equations is omitted.

For better understanding, FP and FN errors will be briefly described with reference to FIGS. 14B and 14C. First, the concept of FP and FN is illustrated in FIG. 14B. FP refers to an error in which a machine learning model outputs a predicted value of "true" even if an actual observed value is "false." On the contrary, FN refers to an error in which the machine learning model outputs the predicted value of "false" even if the actual observed value is "true."

An example of FP will now be briefly described with reference to FIG. 14C. An image 340 shown on the left side of FIG. 14C is a radiographic image of a patient, and an area 341 of the image 340 shows the location of a lesion. In addition, an image 350 shown on the right side of FIG. 14C shows locations 351 and 352 of lesions recognized by a machine learning model based on the image 340.

Here, since the location 351 is the actual location of a lesion, it can be understood as true positive (TP). However, since the location 352 indicates a lesion that does not exist, it can be understood as an FP error. In the medical field using a machine learning model, FP is a major factor that reduces the reliability of equipment. Therefore, it is required to validate a trained object recognition model using a metric such as precision.

Until now, the operation of validating the trained object recognition model has been described with reference to FIGS. 14A through 14C. As described above, the object recognition apparatus 100 according to the inventive concept validates a trained object recognition model by applying a k-fold cross validation technique. Therefore, an object recognition model with more than a certain level of reliability can be provided. The operation recognizing the object of interest in the recognition target image using the trained object recognition model will hereinafter be described with reference to FIGS. 15 and 16.

Object Recognition Method—Recognition

FIG. 15 is a flowchart illustrating the object recognition operation.

Referring to FIG. 15, the object recognition apparatus 100 obtains a recognition target image not given classification results of objects of interest (operation S200). Then, the object recognition apparatus 100 extracts a plurality of feature maps from the recognition target image using learned filters of an object recognition model (operation S210) and matches the sizes of the feature maps (operation S220). The operation of extracting the feature maps (operation S210) and the operation of matching the sizes of the feature maps (operation S220) are the same as the operation of training the object recognition model (operations S110 and S120) and thus are not described to avoid redundancy in description.

Next, the object recognition apparatus 100 generates an activation map for each of the objects of interest by accumulating the matched feature maps (operation S230). Operation S230 is also the same as operation S130 described above, and thus a description of operation S230 is omitted. Finally, the object recognition apparatus 100 recognizes an object of interest included in the recognition target image using the activation maps (operation S240).

As for the operation of recognizing the object of interest included in the recognition target image (operation S240), referring to FIG. 16, the object recognition apparatus 100 amplifies a difference between activation values in the activation maps and calculates a representative value of each object of interest by aggregating the activation values included in a corresponding activation map (operations S242 and S244). As described above, a softmax operation may be used to amplify the difference between values in activation maps, and an LSE operation may be used to calculate a representative value.

Next, the object recognition apparatus 100 determines an object of interest included in the recognition target image using the calculated representative values (operation S246). For example, the object recognition apparatus 100 may compare the calculated representative values and determine an object of interest having a largest representative value to be an object included in the recognition target image. In addition, if a representative value corresponding to the background is largest, the object recognition apparatus 100 may determine that no object of interest exists in the recognition target image.

Next, the object recognition apparatus 100 may determine an area in which the determined object of interest is located in the recognition target image using an activation map of the determined object of interest (operation S238). That is, the object recognition apparatus 100 may determine an area in which core features of the determined object of interest are shown in the activation map of the determined object of interest to be an area in which the determined object of interest is located.

Until now, the operation of recognizing the object of interest in the recognition target image using the trained object recognition model has been described with reference to FIGS. 15 and 16.

The object recognition method described above can be applied to various fields regardless of the type of a recognition target image. For example, the object recognition method may be applied to the medical field in order to produce a pathological diagnosis result including information about the presence or absence of a lesion and the location of the lesion from a radiographic image of a patient.

If applied to the medical field, the inventive concept can provide the following effects. Unlike a supervised learning-based machine learning model, an object recognition model according to the inventive concept does not require a radiographic image tagged with location information of a lesion. Therefore, the time and labor required for a radiologist to tag location information of a lesion in a radiographic image can be reduced significantly. In addition, since the inventive concept utilizes a machine learning-based object recognition model, an accurate pathological diagnosis result can be produced from a radiographic image that is hard to be interpreted even by an expert radiologist due to the limitations of human perception. In addition, since accurate pathological diagnosis results can be produced based on radiographic images that can be acquired at a relatively low cost, the medical cost of patients can be reduced.

The inventive concept described above with reference to FIGS. 6 through 16 can be embodied as computer-readable code on a computer-readable medium. The computer-readable medium may be, for example, a movable recording medium (CD, DVD, blu-ray disc, USE storage device, or movable hard disc) or a fixed recording medium (ROM, RAM, or computer-embedded hard disc). The computer program recorded on the computer-readable recording medium may be transmitted from a first computing device to a second computing device through a network, such as the Internet, to be installed in the second computing device and thus can be used in the second computing device.

While operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various components n the embodiments described above should not be understood as requiring such separation in all embodiments, and it should be understood that the described program components and systems can generally be integrated together in a single software product or packaged into multiple software products.

Experimental Results

Finally, the results of experiments performed using a trained object recognition model will be described briefly.

FIG. 17 illustrates the result of performing object recognition on an image of a 'bicycle.' Specifically, FIG. 17A illustrates a plurality of feature maps extracted by a convolution layer, and FIG. 17B illustrates a plurality of feature maps output from a deconvolution layer corresponding to the convolution layer. A plurality of blobs shown in each of the feature maps indicate areas having feature values which are presented in the form of a heat map.

Referring to FIGS. 17A and 17B, the feature maps of FIG. 17A include more blobs than the feature maps of FIG. 17B. Of the blobs shown in FIG. 17A, blobs only in an area in which the 'bicycle,' i.e., an object of interest is located are included in the feature maps of FIG. 17B.

This indicates that the feature maps of FIG. 17A include a lot of noise unrelated to the 'bicycle.' That is, feature maps output from a deconvolution layer include features only closely related to an object of interest. In other words, an object recognition model constructed using a deconvolution layer as well as a convolution layer is more effective in reducing FP errors than an object recognition model constructed using the convolution layer only.

Figure 18:

FIG. 18 illustrates the result of performing lesion recognition on a chest X-ray (CXR) image. A first column of images in FIG. 18 are original CXR images, and a circular figure indicates the location of a lesion. In addition, a second column of images in FIG. 18 are feature maps extracted by the invention (hereinafter, referred to as cited invention) stated herein as cited literature, and third through fifth columns of images in FIG. 18 are feature maps output from each deconvolution layer according to the present inventive concept. In addition, a plurality of blobs shown in each of the feature maps indicate areas having feature values which are presented in the form of a heat map.

Referring to FIG. 18, feature maps extracted by the cited invention show large blocks in areas other than the location of a lesion in the original images. This indicates that the cited invention is vulnerable to FP errors.

On the other hand, feature maps (deconv-1) extracted by the present inventive concept have smaller blobs than the feature maps extracted by the cited invention. In addition, blobs corresponding to FP errors gradually disappear as the feature maps pass through the deconvolution layers. This indicates that the present inventive concept can provide an object recognition function robust to FP errors as compared with the cited invention.

Until now, the results of experiments performed using the trained object recognition model have been described briefly. According to the experimental results, the present inventive concept can significantly reduce FP errors and thus accurately recognize an area in which an object of interest is located in a given image.

According to the inventive concept, an area in which an object of interest is located in a given image can be accurately recognized using a CNN-based object recognition model composed of a convolution layer and a deconvolution layer. In addition, according to experimental results of the inventive concept, FP errors in which an area in which an object of interest is not located is detected can be reduced significantly.

Also, an activation map is generated by accumulating at least two feature maps among a plurality of feature maps output from a deconvolution layer, and an area in which an object of interest is located is recognized using the activation map. Therefore, the accuracy of object recognition can be improved.

Furthermore, since tied weight matrix values are set for a filter of a convolution layer and a filter of a corresponding deconvolution layer, the complexity of an object recognition model can be reduced, and the object recognition model can be trained more efficiently.

In addition, if applied to the field of medical image-based pathological diagnosis, the inventive concept can provide the following effects.

Unlike a supervised learning-based machine learning model, an object recognition model according to the inventive concept does not require a radiographic image tagged with location information of a lesion. Therefore, the time and labor required for a radiologist to tag location information of a lesion in a radiographic image can be reduced significantly.

In addition, since the inventive concept utilizes a machine learning-based object recognition model, an accurate pathological diagnosis result can be produced from a radiographic image that is hard to be interpreted even by an expert radiologist due to the limitations of human perception.

In addition, since accurate pathological diagnosis results can be produced based on radiographic images that can be acquired at relatively low costs, the medical cost of patients can be reduced.

However, the effects of the inventive concept are not restricted to the one set forth herein. The above and other effects of the inventive concept will become more apparent to one of daily skill in the art to which the inventive concept pertains by referencing the claims.

While the inventive concept has been particularly shown and described with reference to exemplary embodiments thereof, it will be understood by those of ordinary skill in the art that various changes in form and detail may be made therein without departing from the spirit and scope of the inventive concept as defined by the following claims. The exemplary embodiments should be considered in a descriptive sense only and not for purposes of limitation.

What is claimed is:

1. An object recognition method based on weakly supervised learning, the method performed by an object recognition apparatus and comprising:
    extracting a plurality of feature maps from a training target image given classification result of an object of interest;
    generating an activation map for each of the object of interest by accumulating the feature maps;
    calculating a representative value of each of the object of interest by aggregating activation values included in a corresponding activation map;
    determining an error by comparing classification result determined using the representative value of each of the object of interest with the given classification result; and
    updating a convolutional neural network (CNN)-based object recognition model by back-propagating the error,
    wherein the generating of the activation map comprises:
        determining an activation value at a first location in the activation map using feature values at the first location in the feature maps; and
        determining an activation value at a second location in the activation map using feature values at the second location in the feature maps, and
    wherein the activation map is an activation map of a first object of interest, and the determining of the activation value at the first location in the activation map comprises adjusting the activation value at the first location in the activation map of the first object of interest to increase a difference between the activation value at the first location in the activation map of the first object of interest and an activation value at the first location in an activation map of a second object of interest different from the first object of interest.

2. The method of claim 1, wherein the object recognition model comprises:
    a convolution layer which extracts a plurality of feature maps from the training target image; and
    a deconvolution layer which increases sizes of the feature maps while maintaining a pattern shown in the feature maps.

3. The method of claim 2, wherein the deconvolution layer is provided in a plurality, and the feature maps comprise at least two feature maps among feature maps input to the deconvolution layers and feature maps output from the deconvolution layers.

4. The method of claim 2, wherein the feature maps comprise a plurality of feature maps having different sizes, and the generating of the activation map comprises matching the sizes of the feature maps and generating an activation map for each of the object of interest using the matched feature maps.

5. The method of claim 2, wherein a weight matrix of a filter used in the deconvolution layer is obtained by transposing a weight matrix of a filter used in the convolution layer corresponding to the deconvolution layer.

6. The method of claim 1, wherein the training target image is a radiographic image, and the object of interest is a lesion.

7. An object recognition apparatus comprising:
one or more processors;
a network interface;
a memory which loads a computer program executed by the processors to perform an object recognition method based on weakly supervised learning; and
a storage which stores the computer program,
wherein the computer program comprises:
an operation of extracting a plurality of feature maps from a training target image given classification result of an object of interest;
an operation of generating an activation map for each of the object of interest by accumulating the feature maps;
an operation of calculating a representative value of each of the object of interest by aggregating activation values included in a corresponding activation map;
an operation of determining an error by comparing classification result determined using the representative value of each of the object of interest with the given classification result; and
an operation of updating a convolutional neural network (CNN)-based object recognition model by back-propagating the error,
wherein the operation of generating of the activation map comprises:
an operation of determining an activation value at a first location in the activation map using feature values at the first location in the feature maps; and
an operation of determining an activation value at a second location in the activation map using feature values at the second location in the feature maps, and
wherein the activation map is an activation map of a first object of interest, and the operation of determining of the activation value at the first location in the activation map comprises an operation of adjusting the activation value at the first location in the activation map of the first object of interest to increase a difference between the activation value at the first location in the activation map of the first object of interest and an activation value at the first location in an activation map of a second object of interest different from the first object of interest.

8. The apparatus of claim 7, wherein the object recognition model comprises:
a convolution layer which extracts a plurality of feature maps from the training target image; and
a deconvolution layer which increases sizes of the feature maps while maintaining a pattern shown in the feature maps.

9. The apparatus of claim 8, wherein the deconvolution layer is provided in a plurality, and the feature maps comprise at least two feature maps among feature maps input to the deconvolution layers and feature maps output from the deconvolution layers.

10. The apparatus of claim 8, wherein the feature maps comprise a plurality of feature maps having different sizes, and the operation of generating of the activation map comprises an operation of matching the sizes of the feature maps and an operation of generating an activation map for each of the object of interest using the matched feature maps.

11. The apparatus of claim 8, wherein a weight matrix of a filter used in the deconvolution layer is obtained by transposing a weight matrix of a filter used in the convolution layer corresponding to the deconvolution layer.

* * * * *